(12) United States Patent
Ichikawa

(10) Patent No.: US 9,880,106 B2
(45) Date of Patent: Jan. 30, 2018

(54) VEHICLE LAMP DEVICE AND ABNORMALITY DETECTOR OF LIGHT SOURCE THEREOF

(71) Applicant: KOITO MANUFACTURING CO., LTD., Tokyo (JP)

(72) Inventor: Tomoyuki Ichikawa, Shizuoka (JP)

(73) Assignee: KOITO MANAUFACTURING CO., LTD., Tokyo (JP)

( * ) Notice: Subject to any disclaimer, the term of this patent is extended or adjusted under 35 U.S.C. 154(b) by 167 days.

(21) Appl. No.: 14/845,918

(22) Filed: Sep. 4, 2015

(65) Prior Publication Data

US 2016/0069819 A1    Mar. 10, 2016

(30) Foreign Application Priority Data

Sep. 4, 2014   (JP) .................................. 2014-179881
Jan. 14, 2015   (JP) .................................. 2015-005214

(51) Int. Cl.
 *H02H 3/00* (2006.01)
 *G01N 21/95* (2006.01)
 (Continued)

(52) U.S. Cl.
 CPC .......... *G01N 21/95* (2013.01); *F21S 48/1145* (2013.01); *G01N 21/4788* (2013.01);
 (Continued)

(58) Field of Classification Search
 USPC .............................................. 361/23, 86–87
 See application file for complete search history.

(56) References Cited

U.S. PATENT DOCUMENTS

2009/0153855 A1\* 6/2009 Bungo ...................... G01J 3/02
                                                                 356/319
2011/0063115 A1\* 3/2011 Kishimoto ................ F21K 9/00
                                                                 340/600
(Continued)

FOREIGN PATENT DOCUMENTS

EP    2204856 A1   7/2010
EP    2244004 A2  10/2010
(Continued)

OTHER PUBLICATIONS

Extended European Search Report issued in corresponding European Application No. 15183733.3, dated Feb. 19, 2016 (8 pages).

*Primary Examiner* — Danny Nguyen
(74) *Attorney, Agent, or Firm* — Osha Liang LLP

(57) ABSTRACT

An abnormality detector for a light source includes a laser diode which emits an excitation light and a fluorescent substance which is excited by the excitation light to generate a fluorescent light. The abnormality detector includes a first photo sensor which is sensitive to a wavelength of the excitation light, a second photo sensor which is sensitive to a wavelength of the fluorescent light, a first current-voltage conversion circuit which outputs a first detection signal based on an output of the first photo sensor, a second current-voltage conversion circuit which outputs a second detection signal based on an output of the second photo sensor, and a determination unit which determines whether an abnormality occurs based on the first detection signal and the second detection signal.

20 Claims, 16 Drawing Sheets

(51) Int. Cl.
*F21S 8/10* (2006.01)
*H02H 7/20* (2006.01)
*G01N 21/47* (2006.01)
*G01N 21/64* (2006.01)
*H05B 37/03* (2006.01)
*H01S 5/00* (2006.01)
*H01S 5/068* (2006.01)

(52) U.S. Cl.
CPC ............ *G01N 21/645* (2013.01); *H02H 7/20* (2013.01); *G01N 2201/0612* (2013.01); *H01S 5/0092* (2013.01); *H01S 5/06825* (2013.01); *H05B 37/03* (2013.01)

(56) References Cited

U.S. PATENT DOCUMENTS

| | | | |
|---|---|---|---|
| 2011/0084609 A1* | 4/2011 | Kawaguchi | F21V 9/16 315/77 |
| 2012/0019786 A1 | 1/2012 | Kimura | |
| 2014/0009952 A1* | 1/2014 | Nomura | F21S 48/1159 362/509 |

FOREIGN PATENT DOCUMENTS

| JP | 2004-241142 A | 8/2004 |
|---|---|---|
| WO | 2010/070720 A1 | 6/2010 |
| WO | 2014125782 A1 | 8/2014 |

* cited by examiner

30c

30d

56

56

VEHICLE LAMP DEVICE AND ABNORMALITY DETECTOR OF LIGHT SOURCE THEREOF

CROSS-REFERENCE TO RELATED APPLICATIONS

The present application claims the benefit of priority of Japanese Patent Application No. 2014-179881, filed on Sep. 4, 2014 and Japanese Patent Application No. 2015-005214, filed on Jan. 14, 2015, the content of which is incorporated herein by reference.

TECHNICAL FIELD

Aspects of the present invention relate to a vehicle lamp device to be used for an automobile and the like.

BACKGROUND

Conventionally, a vehicle lamp device, particularly, a head lamp, mainly uses a halogen lamp or a High Intensity Discharge (HID) lamp as a light source. In recent years, however, a vehicle lamp device using a semiconductor light source such as a Light Emitting Diode (LED) has been developed.

In order to further improve visibility, for example, JP-A-2004-241142 discloses a vehicle lamp device including a laser diode (also referred to as a semiconductor laser) and a fluorescent substance, instead of an LED. In this vehicle lamp device, an ultraviolet light which is an excitation light emitted from the laser diode is emitted to the fluorescent substance. The fluorescent substance receives the ultraviolet light and generates a white light. The white light generated by the fluorescent substance is emitted to the front of the lamp device such that a predetermined light distribution pattern is formed. In this vehicle lamp device, the excitation light is not emitted to the front.

SUMMARY

FIG. 1 is a sectional view of a light source of a vehicle lamp device examined by the inventor of the present invention. The light source 10 includes a laser diode 12, a fluorescent substance 14, an optical system 16 and a housing 18. The light source 10 is similar to the vehicle lamp device disclosed in JP-A-2004-241142 in that it has the laser diode 12 and the fluorescent substance 14.

The laser diode 12 is configured to generate a blue excitation light 20 (not an ultraviolet light). The excitation light 20 is concentrated on the fluorescent substance 14 by the optical system 16. The optical system 16 is configured by a lens, a reflector, an optical fiber or a combination thereof. The fluorescent substance 14 having received the blue excitation light 20 generates a fluorescent light 22 having a spectral distribution in a wavelength region (green to red) longer than the excitation light 20. The excitation light 20 emitted to the fluorescent substance 14 is scattered by the fluorescent substance 14 and passes through the fluorescent substance 14 with coherence thereof being lost. The fluorescent substance 14 is fitted and supported to an opening formed in the housing 18, for example.

FIG. 2 shows a spectrum of an output light 24 of the light source 10. The output light 24 of the light source 10 includes a blue excitation light 20a having passed through the fluorescent substance 14 and green to red fluorescent light 22 generated by the fluorescent substance 14 and has a spectral distribution of the white light.

That is, while the ultraviolet excitation light is not used as a part of the emission light illuminating the front of the vehicle in the vehicle lamp device of JP-A-2004-241142, the blue excitation light is used as a part of the emission light of the head lamp in the light source 10 of FIG. 1.

The inventor of the present invention studied on the light source 10 of FIG. 1 and recognized following problems. In the light source 10 of FIG. 1, when an abnormality such as breaking of the fluorescent substance 14 or removal of the fluorescent substance 14 from the housing 18 occurs, the excitation light 20 generated by the laser diode 12 is directly emitted to the front of the vehicle with the strong coherence and without being scattered by the fluorescent substance 14, which is dangerous.

The present invention has been made in view of the above circumstances, and an aspect of the present invention provides a technique capable of securely detecting an abnormality in a light source having a combination of a blue laser diode and a fluorescent substance.

(First Aspect)

According to a first aspect of the present invention, there is provided an abnormality detector for a light source. The light source includes a laser diode configured to emit an excitation light and a fluorescent substance configured to be excited by the excitation light to generate a fluorescent light, and is configured to generate a white output light having spectra of the excitation light and the fluorescent light. The abnormality detector includes a first photo sensor which is sensitive to a wavelength of the excitation light and substantially insensitive to a wavelength of the fluorescent light and which is configured to receive a part of the output light to generate a first current in accordance with an amount of the received light, a second photo sensor which is sensitive to the wavelength of the fluorescent light and substantially insensitive to the wavelength of the excitation light and which is configured to receive a part of the output light to generate a second current in accordance with an amount of the received light, a first current-voltage conversion circuit which includes a first resistance provided on a path of the first current and which is configured to output a first detection signal corresponding to a voltage drop of the first resistance, a second current-voltage conversion circuit which includes a second resistance provided on a path of the second current and which is configured to output a second detection signal corresponding to a voltage drop of the second resistance, and a determination unit which is configured to determine whether an abnormality occurs based on the first detection signal and the second detection signal.

The first detection signal linearly changes in accordance with an amount of light of the excitation light, and a gradient thereof is determined in accordance with a resistance value of the first resistance. Similarly, the second detection signal linearly changes in accordance with an amount of light of the fluorescent light, and a gradient thereof is determined in accordance with a resistance value of the second resistance. Here, when the fluorescent substance is normal, an intensity of the excitation light, an intensity of the fluorescent light and an intensity of the white light, which is an output of the light source, are proportional to each other. Therefore, when the fluorescent substance is normal, a ratio of the first detection signal and the second detection signal is substantially constant, and when an abnormality occurs in the fluorescent substance and the excitation light is thus directly emitted, a balance of the excitation light and fluorescent light included in the output light is lost, so that the ratio of the first detection signal and the second detection signal changes. According to the above configuration, it is possible to simply and securely detect the abnormality of the fluorescent substance by appropriately determining the resistance values of the first resistance and the second resistance and monitoring the first detection signal and the second detection signal, irrespective of an intensity of the white light, i.e., an output of the light source.

In the above abnormality detector, in a case where the first current is denoted as I1 and the second current is denoted as I2 when the fluorescent substance is normal, and the first current is denoted as I1' and the second current is denoted as I2' when the fluorescent substance is abnormal, a resistance value R1 of the first resistance and a resistance value R2 of the second resistance may satisfy the following relation equations:

$$R1 \times I1 < R2 \times I2 \quad (1); \text{ and}$$

$$R1 \times I1' > R2 \times I2' \quad (2).$$

In this case, it is possible to detect whether an abnormality occurs by comparing magnitudes of the first detection signal and the second detection signal.

In the above abnormality detector, the determination unit may be configured to determine that an abnormality occurs when a magnitude relation of the first detection signal and the second detection signal is reversed.

In the above abnormality detector, the determination unit may include a voltage comparator.

In the above abnormality detector, the first current-voltage conversion circuit may include a first operational amplifier having an inverting input terminal to which the first photo sensor is connected and a non-inverting input terminal to which a fixed voltage is applied, and the first resistance provided between the inverting input terminal and an output terminal of the first operational amplifier. The second current-voltage conversion circuit may include a second operational amplifier having an inverting input terminal to which the second photo sensor is connected and a non-inverting input terminal to which a fixed voltage is applied, and the second resistance provided between the inverting input terminal and an output terminal of the second operational amplifier.

In this configuration, gains (current-voltage conversion) of the first current-voltage conversion circuit and the second current-voltage conversion circuit are determined only by the resistance values of the first resistance and the second resistance. Thereby, it is possible to exclude an error factor, so that it is possible to detect an abnormality with high precision.

In the above abnormality detector, the first photo sensor may include a first photo diode, and the second photo sensor may include a second photo diode. A cathode of the first photo diode may be connected to the inverting input terminal of the first operational amplifier and a fixed voltage may be applied to an anode of the first photo diode. A cathode of the second photo diode may be connected to the inverting input terminal of the second operational amplifier and a fixed voltage may be applied to an anode of the second photo diode.

In this case, since a voltage is not applied between the anode and cathode of the photo diode, it is possible to detect the light without an influence of a dark current in a wide range of the amount of light.

In the above abnormality detector, the first photo sensor may include a first photo diode, and the second photo sensor may include a second photo diode. The inverting input terminal of the first operational amplifier may be connected with an anode of the first photo diode, and the non-inverting input terminal of the first operational amplifier may be connected with a cathode of the first photo diode and is applied with a fixed voltage. The inverting input terminal of the second operational amplifier may be connected with an anode of the second photo diode, and the non-inverting input terminal of the second operational amplifier may be connected with a cathode of the second photo diode and may be applied with a fixed voltage.

In the above abnormality detector, the determination unit may be configured to offset at least one of the first detection signal and the second detection signal in a direction of separating from each other.

When the output of the light source is low, the first detection signal and the second detection signal are close to each other, so that a false detection may be caused due to an influence of the noise. If an offset is used, it is possible to suppress the abnormal false detection when the amount of light is small.

In the above abnormality detector, the determination unit may include a voltage-dividing circuit configured to voltage-divide the second detection signal. Thereby, it may be possible to provide the offset by the simple configuration of only the two resistances. In the meantime, at this time, when the output of the light source is greater than a predetermined value, the influence resulting from the setting of the voltage-dividing circuit, i.e., an influence resulting from the usage of the offset is suppressed and the precision of the abnormality detection can be kept.

According to another aspect of the present invention, there is provided a vehicle lamp device. The vehicle lamp device includes a light source, the above abnormality detector which is configured to detect an abnormality of the light source; and a lighting circuit which is configured to drive the light source and to execute predetermined protection processing when the abnormality detector detects an abnormality of the light source.

In the above vehicle lamp device, a plurality of the abnormality detectors may be provided, and the lighting circuit may execute the protection processing when at least one the abnormality detectors detects an abnormality.

In this case, even when a failure or abnormality occurs in any one abnormality detector, it is possible to detect the abnormality of the light source by the separate abnormality detector and to execute the appropriate protection processing.

(Second Aspect)

According to a second aspect of the present invention, there is provided an abnormality detector for a light source. The light source includes a laser diode configured to emit an excitation light and a fluorescent substance configured to be excited by the excitation light to generate a fluorescent light, and which is configured to generate a white output light having spectra of the excitation light and the fluorescent light. The abnormality detector includes a diffraction element which is configured to diffract the output light of the light source, a light detector which is configured to detect a diffracted light by the diffraction element, and a determination unit which is configured to determine whether an abnormality occurs based on a detection result of the light detector.

When the fluorescent substance is normal, the excitation light is scattered by the fluorescent substance. Therefore, the excitation light incident to the diffraction element is lowered in coherency, so that a substantial interference fringe (interference fringe) is not observed in the diffracted light obtained by the diffraction element. On the other hand, when the fluorescent substance is abnormal, the excitation light is not scattered and is highly-coherently incident to the diffraction element. Therefore, the substantial interference fringe is observed in the diffracted light obtained by the diffraction element. Therefore, according to the second aspect, it is possible to determine whether the fluorescent substance is abnormal based on the diffracted light of the diffraction element.

In the above abnormality detector, the light detector may be configured to detect light intensities of two positions including a first position at which a pattern of the diffracted light has a peak when the fluorescent substance is normal and a second position at which there is no peak when the fluorescent substance is normal, and the determination unit may be configured to determine whether an abnormality occurs based on the light intensities of the two positions.

In the above abnormality detector, the light detector may include two photo sensors provided at the two positions, and the determination unit may be configured to determine that an abnormality occurs when a difference of outputs of the two photo sensors exceeds a predetermined threshold.

In the above abnormality detector, the light detector may include a plurality of pixels configured to receive the diffracted light, and the determination unit may be configured to determine whether an abnormality occurs based on a diffraction pattern measured by the plurality of pixels.

In the above abnormality detector, the determination unit may include a differentiator configured to spatially differentiate data measured by the plurality of pixels, and the determination unit may be configured to determine whether occurs an abnormality based on an output of the differentiator. Thereby, it is possible to determine whether the substantial diffraction pattern occurs.

In the above abnormality detector, the data from the plurality of pixels may be sequentially read, the differentiator may be configured to temporally differentiate the data sequentially read from the plurality of pixels, and the determination unit may be configured to determine that an abnormality occurs when the output of the differentiator exceeds a predetermined threshold.

The above abnormality detector may further include a pinhole provided between the diffraction element and the light source. Thereby, when the fluorescent substance is abnormal, it is possible to obtain a clear diffraction pattern.

In the above abnormality detector, the light source and the abnormality detector may be used for a vehicle lamp device, the vehicle lamp device may include a reflector configured to reflect the output light of the light source, and the reflector may be formed with the pinhole.

According to another aspect of the present invention, there is provided a vehicle lamp device. The vehicle lamp device includes a light source and the above abnormality detector which is configured to detect an abnormality of the light source.

According to the above configuration, it is possible to detect an abnormality of the fluorescent substance.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Figure 1:
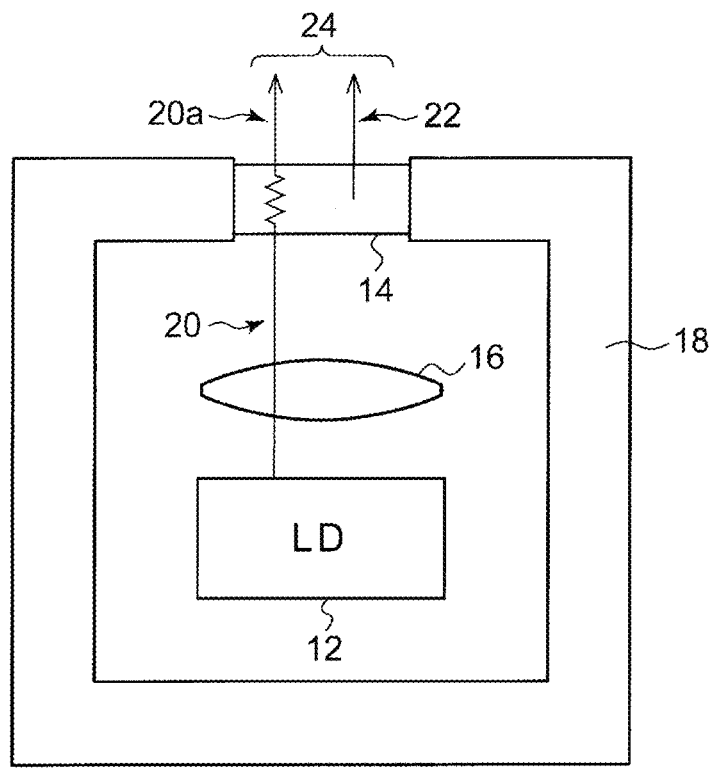
FIG. 1 is a sectional view of a light source of a vehicle lamp device examined by the inventor.
Figure 2:
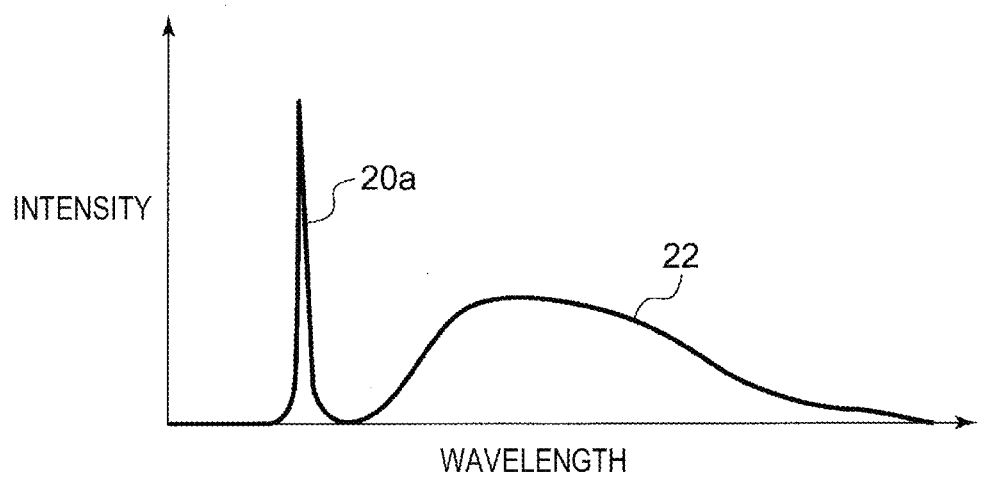
FIG. 2 shows a spectrum of an output light of the light source.

Illustrative embodiments will be described below with reference to the accompanying drawings. Constituent elements, members and/or steps which are shown in the drawings and which are the same as or equivalent to each other may be given the same reference signs. Also, redundant description thereon may be omitted accordingly. It should be noted that the illustrative embodiments described below do not limit the scope of the invention and are just exemplary or illustrative. All of features described below or any combination thereof may not be always essential for the present invention.

In this specification, the description "a state where a member A is connected to a member B" includes not only a case where the member A and the member B are physically directly connected but also a case where the member A and the member B are indirectly connected via another member, which does not substantially influence electrical connection states thereof or does not damage functions and effects exhibited by the connection thereof.

Similarly, the description "a state where a member C is provided between a member A and a member B" includes not only a case where the member A and the member C or the member B and the member C are directly connected but also a case where the member A and the member C or the member B and the member C are indirectly connected via another member, which does not substantially influence electrical connection states thereof or does not damage functions and effects exhibited by the connection thereof.

Also, in this specification, the reference numerals denoted at an electric signal such as a voltage signal and a current signal, and a circuit element such as a resistance and a capacitor may indicate a voltage value, a current value, a resistance value and a capacitance.

First Illustrative Embodiment

Figure 3:
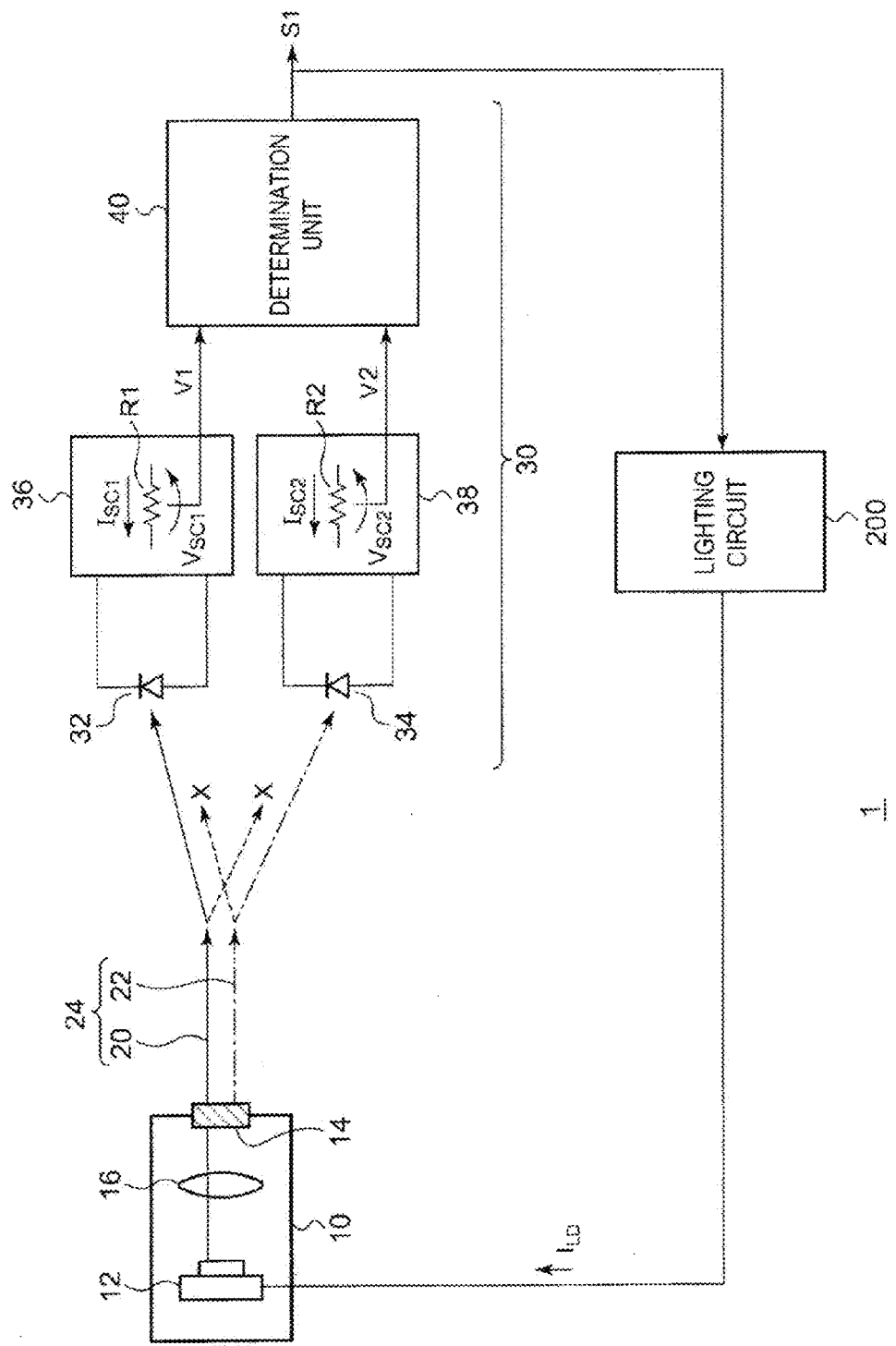
FIG. 3 is a block diagram of a vehicle lamp device having an abnormality detector according to a first illustrative embodiment.

FIG. 3 is a block diagram of a vehicle lamp device 1 having an abnormality detector 30 according to a first illustrative embodiment. The vehicle lamp device 1 includes a light source 10, the abnormality detector 30 configured to detect an abnormality of the light source 10 and a lighting circuit 200.

As described with reference to FIG. 1, the light source 10 includes a laser diode 12, a fluorescent substance 14 and an optical system 16. The laser diode 12 is configured to emit an excitation light 20. The laser diode 12 is configured to emit the light with an intensity corresponding to a driving current supplied from a driving circuit (not shown). The fluorescent substance 14 is provided on a light path of the excitation light 20 and is excited by the excitation light 20 to generate a fluorescent light 22. The light source 10 is configured to generate a white output light 24 including spectra of the excitation light 20 and the fluorescent light 22.

The lighting circuit 200 is configured to supply a driving current $I_{LD}$ to the laser diode 12 and to enable the laser diode 12 to emit the light. A configuration of the lighting circuit 200 is not particularly limited and a known configuration may be used.

The abnormality detector 30 is configured to receive a part of the output light 24 and to determine whether the light source 10 is abnormal, more specifically, whether the fluorescent substance 14 is abnormal. The abnormality of the fluorescent substance 14 may be, for example, breaking, removal, aging deterioration and the like of the fluorescent substance 14, but not limited to those. When the abnormality detector 30 detects an abnormality, the abnormality detector 30 asserts an abnormality detection signal S1 (for example, changes into a high level). When the abnormality detector 30 detects an abnormality, the lighting circuit 200 executes predetermined protection processing. The protection processing may include light-off of the laser diode 12, reduction in brightness (an amount of light), notifications to various upper Electronic Control Units (ECUs) and the like, but not limited to those.

The abnormality detector 30 includes a first photo sensor 32, a second photo sensor 34, a first current-voltage conversion circuit 36, a second current-voltage conversion circuit 38 and a determination unit 40. The first photo sensor 32 is sensitive to a wavelength of the excitation light 20 and is substantially insensitive to a wavelength of the fluorescent light 22. The first photo sensor 32 is configured to receive a part of the output light 24 to generate a first current $I_{SC1}$ in accordance with the intensity of the excitation light 20 having passed through the fluorescent substance 14. The second photo sensor 34 is sensitive to the wavelength of the fluorescent light 22 and is substantially insensitive to the wavelength of the excitation light 20. The second photo sensor 34 is configured to receive a part of the output light 24 to generate a second current $I_{SC2}$ in accordance with the intensity of the fluorescent light 22 generated by the fluorescent substance 14.

The wavelength selectivity to which the first photo sensor 32 and the second photo sensor 34 are respectively sensitive may be implemented by a color filter, a semiconductor material of a sensor or a device structure. The first photo sensor 32 and the second photo sensor 34 are not particularly limited, and semiconductor light sensors such as photo diodes and photo transistors may be used. In this illustrative embodiment, the first photo sensor 32 and the second photo sensor 34 include the photo diodes, respectively.

The first current-voltage conversion circuit 36 includes a first resistance R1 provided on a path of the first current $I_{SC1}$ and is configured to output a first detection signal V1 corresponding to a voltage drop $V_{SC1}$ of the first resistance R1. The first detection signal V1 linearly changes with respect to the first current $I_{SC1}$ with a gradient corresponding to a resistance value of the first resistance R1.

The second current-voltage conversion circuit 38 includes a second resistance R2 provided on a path of the second current $I_{SC2}$ and is configured to output a second detection signal V2 corresponding to a voltage drop $V_{SC2}$ of the second resistance R2. The second detection signal V2 linearly changes with respect to the second current $I_{SC2}$ with a gradient corresponding to a resistance value of the second resistance R2.

The determination unit 40 is configured to determine whether an abnormality occurs based on the first detection signal V1 and the second detection signal V2. When an abnormality is detected, the determination unit 40 asserts the abnormality detection signal S1 (for example, changes into a high-level). The above is the basic configuration of the abnormality detector 30. Subsequently, an operation principle thereof is described.

The first detection signal V1 linearly changes in accordance with an amount of light of the excitation light 20, and the gradient thereof is determined in accordance with the resistance value of the first resistance R1. Similarly, the second detection signal V2 linearly changes in accordance with an amount of light of the fluorescent light 22, and the gradient thereof is determined in accordance with the resistance value of the second resistance R2. Here, when the fluorescent substance 14 is normal, an intensity of the excitation light 20, an intensity of the fluorescent light 22 and an intensity of the output light 24 of the light source 10 are proportional to each other. Therefore, when the fluorescent substance 14 is normal, a ratio of the first detection signal V1 and the second detection signal V2 is substantially constant. In contrast, when the fluorescent substance 14 is abnormal and the excitation light 20 is thus directly emitted, a balance of the excitation light 20 and fluorescent light 22 included in the output light 24 is lost, so that the ratio of the first detection signal V1 and the second detection signal V2 changes. According to the abnormality detector 30 of FIG. 3, it is possible to simply and securely detect the abnormality of the fluorescent substance 14 by appropriately determining the resistance values of the first resistance R1 and the second resistance R2 and monitoring the first detection signal V1 and the second detection signal V2, irrespective of an intensity of the white light, i.e., an output of the light source.

Figure 4A:
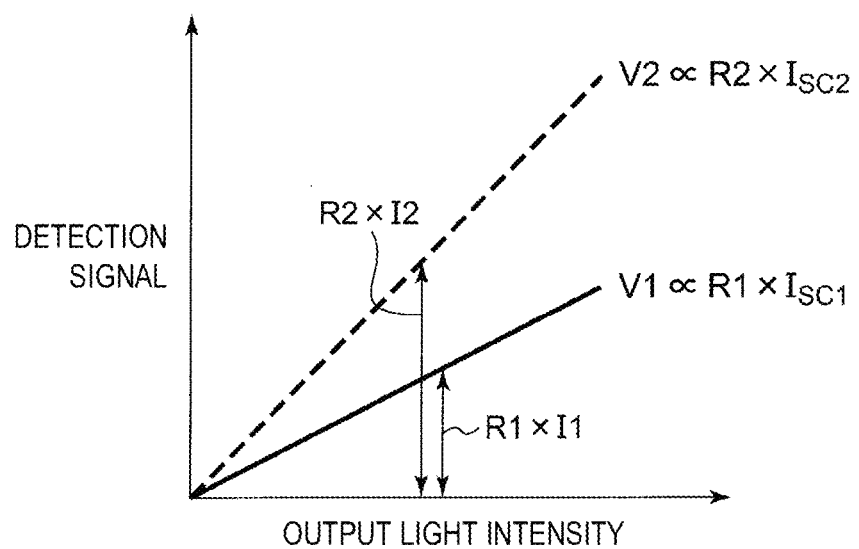
FIG. 4A shows a relation among an output light intensity, a first detection signal and a second detection signal when a fluorescent substance is normal.
Figure 4B:
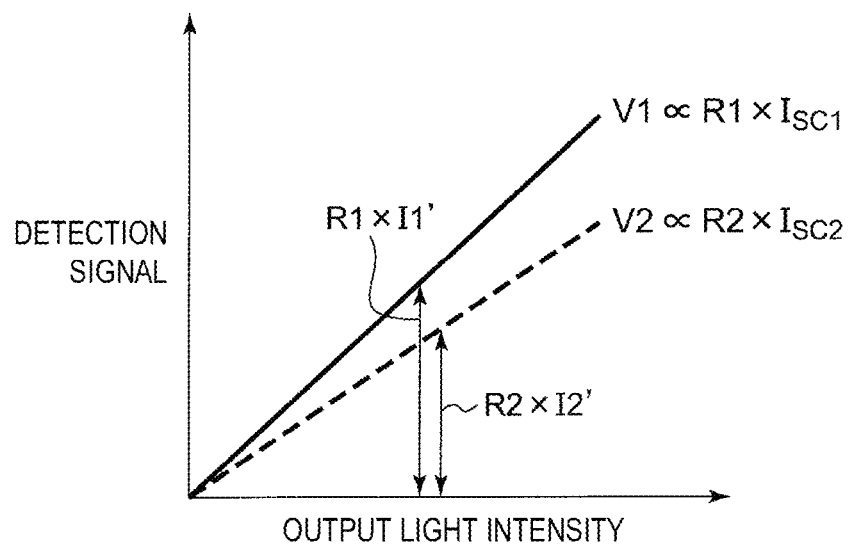
FIG. 4B shows the relation among the output light intensity, the first detection signal and the second detection signal when the fluorescent substance is abnormal.

FIG. 4A shows a relation among an output light intensity, the first detection signal V1 and the second detection signal V2 when the fluorescent substance 14 is normal, and FIG. 4B shows a relation among the output light intensity, the first detection signal V1 and the second detection signal V2 when the fluorescent substance 14 is abnormal.

When the fluorescent substance 14 is normal, the first current $I_{SC1}$ is denoted as I1 and the second current $I_{SC2}$ is denoted as I2 at an output light intensity, and when the fluorescent substance 14 is abnormal, the first current $I_{SC1}$ is denoted as I1' and the second current $I_{SC2}$ is denoted as I2'. When an abnormality occurs in the fluorescent substance 14, the intensity of the fluorescent light 22 decreases and the excitation light 20 passes without being absorbed by the fluorescent light 22, so that I1' becomes larger than I1 and I2' becomes smaller than I2. At this time, the resistance value of the first resistance R1 and the resistance value of the second resistance R2 are preferably determined to meet following relation equations.

$$R1 \times I1 < R2 \times I2 \quad (1)$$

$$R1 \times I1' > R2 \times I2' \quad (2)$$

The abnormality detector 30 compares a magnitude relation of the first detection signal V1 and the second detection signal V2 and determines that an abnormality occurs when the magnitude relation is reversed. The processing of the abnormality detector 30 is equivalent to processing of comparing a ratio $I_{SC1}/I_{SC2}$ of the detection current $I_{SC1}$ of the first photo sensor 32 and the detection current $I_{SC2}$ of the second photo sensor 34 and a ratio R2/R1 of the resistance values of the first resistance R1 and the second resistance R2. The abnormality detector 30 may determine that an abnormality occurs when a ratio $I_{SC1}/I_{SC2}$ of the intensity of the blue excitation light 20 and the intensity of the yellow fluorescent light exceeds a predetermined determination value (R2/R1).

The scope of the present invention includes various circuits which can be perceived from the block diagram of FIG. 3. In the below, specific configuration examples are described.

First Configuration Example

Figure 5:
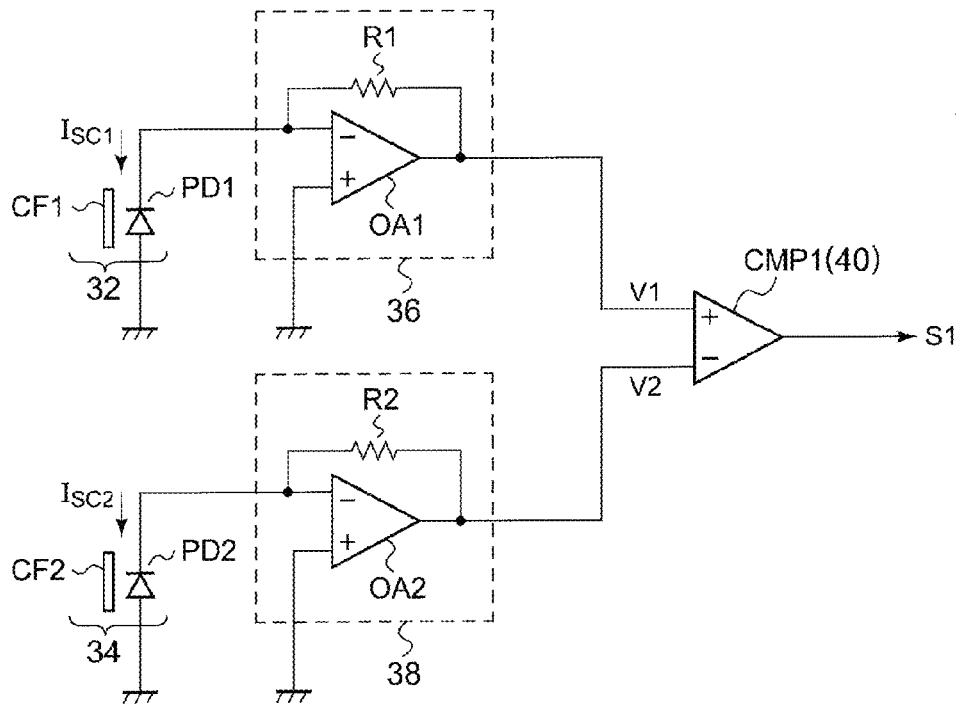
FIG. 5 is a circuit diagram showing an abnormality detector according to a first configuration example.

FIG. 5 is a circuit diagram showing an abnormality detector 30A according to a first configuration example.

In this configuration example, the first photo sensor 32 includes a first photo diode PD1 and a first color filter CF1. The first color filter CF1 is configured such that a transmittance thereof is high with respect to a blue light having the wavelength of the excitation light 20 and is low with respect to the wavelength of the fluorescent light 22. The second photo sensor 34 includes a second photo diode PD2 and a second color filter CF2. The second color filter CF2 is configured such that a transmittance thereof is high with respect to green to red light in the wavelength region of the fluorescent light 22 and is low with respect to the blue light. As the first color filter CF1, a blue filter may be used, and as the second color filter CF2, a yellow filter, a green filter or a red filter may be used.

The first current-voltage conversion circuit 36 includes a first operational amplifier OA1 in addition to the first resistance R1. The first photo sensor 32 is connected to an inverting input terminal (−) of the first operational amplifier OA1 and a fixed voltage is applied to a non-inverting input terminal (+). The fixed voltage is a ground voltage, for example. The first resistance R1 is provided between the inverting input terminal (−) and an output terminal of the first operational amplifier OA1.

More specifically, a cathode of the first photo diode PD1 of the first photo sensor 32 is connected to the inverting input terminal (−) of the first operational amplifier OA1, and the fixed voltage (ground voltage) is applied to an anode of the first photo diode PD1.

A voltage of the first detection signal V1 generated by the first current-voltage conversion circuit 36 is expressed by an equation (3).

$$V1 = R1 \times I_{SC1} \quad (3)$$

The second current-voltage conversion circuit 38 includes a second operational amplifier OA2 in addition to the second resistance R2 and is configured similarly to the first current-voltage conversion circuit 36, and a voltage of the output V2 thereof is expressed by an equation (4).

$$V2 = R2 \times I_{SC2} \quad (4)$$

The determination unit 40 includes a voltage comparator CMP1 configured to compare the voltages of the first detection signal V1 and the second detection signal V2. The abnormality detection signal S1 which is output from the voltage comparator CMP1 is a low level (negate) when V1<V2, i.e., the fluorescent substance 14 is normal, and is a high level (assert) when V1>V2, i.e., the fluorescent substance 14 is abnormal.

The abnormality detector 30a of FIG. 5 may be configured as a small-scale circuit including two operational amplifiers, two resistances and one comparator, in addition to the two photo diodes. A current-voltage conversion gain (transimpedance) of each of the first current-voltage conversion circuit 36 and the second current-voltage conversion circuit 38 depends only on the first resistance R1 and the second resistance R2. Therefore, it is possible to reduce an influence of variation of elements, so that it is possible to detect the abnormality with high precision.

Further, according to the first current-voltage conversion circuit 36 of FIG. 5, due to the virtual ground of the first operational amplifier OA1, the ground voltage is applied to each of the anode and cathode of the first photo diode PD1 such that a potential difference between the anode and cathode of the first photo diode PD1 becomes substantially zero. Therefore, it is possible to detect the light without an influence of a dark current in a wide range of the amount of light. The second current-voltage conversion circuit 38 is also the same.

Second Configuration Example

Figure 6:
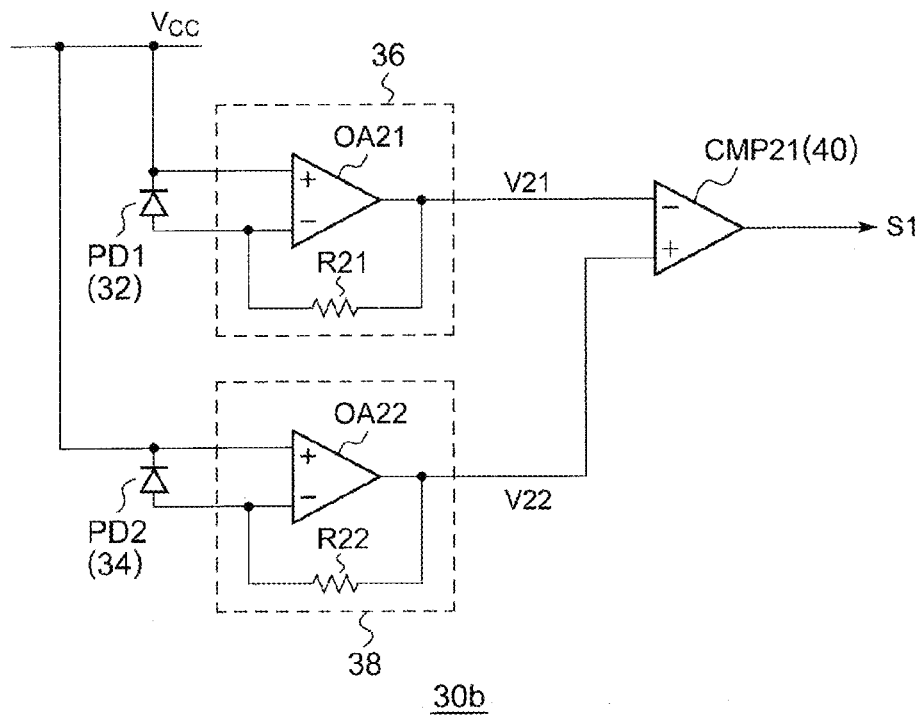
FIG. 6 is a circuit diagram showing an abnormality detector according to a second configuration example.

FIG. 6 is a circuit diagram showing an abnormality detector 30b according to a second configuration example.

Regarding the first current-voltage conversion circuit 36, an inverting input terminal (−) of a first operational amplifier OA21 is connected with the anode of the first photo diode PD1, and a non-inverting input terminal (+) of the first operational amplifier OA21 is connected with the cathode of the first photo diode PD1 and is applied with a predetermined fixed voltage. For example, the fixed voltage may be a power supply voltage $V_{CC}$, or the other voltage.

A voltage of a first detection signal V21 generated by the first current-voltage conversion circuit 36 of FIG. 6 is expressed by an equation (5).

$$V21 = V_{CC} - R21 \times I_{SC1} \qquad (5)$$

The second current-voltage conversion circuit 38 is configured similarly to the first current-voltage conversion circuit 36, and a voltage of an output V22 thereof is expressed by an equation (6).

$$V21 = V_{CC} - R22 \times I_{SC2} \qquad (6)$$

Figure 7A:
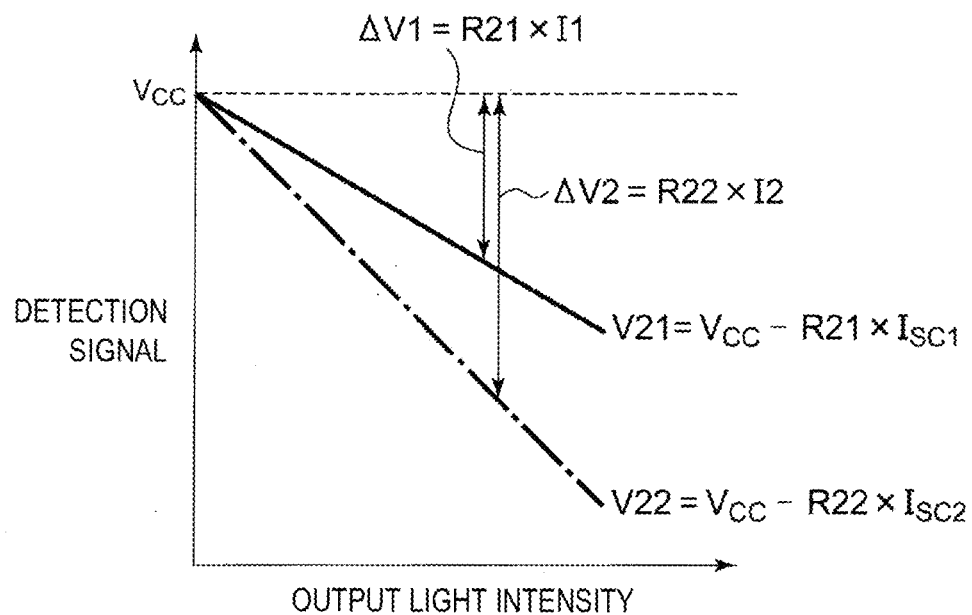
FIG. 7A shows a relation among the output light intensity, the first detection signal and the second detection signal when the fluorescent substance is normal.
Figure 7B:
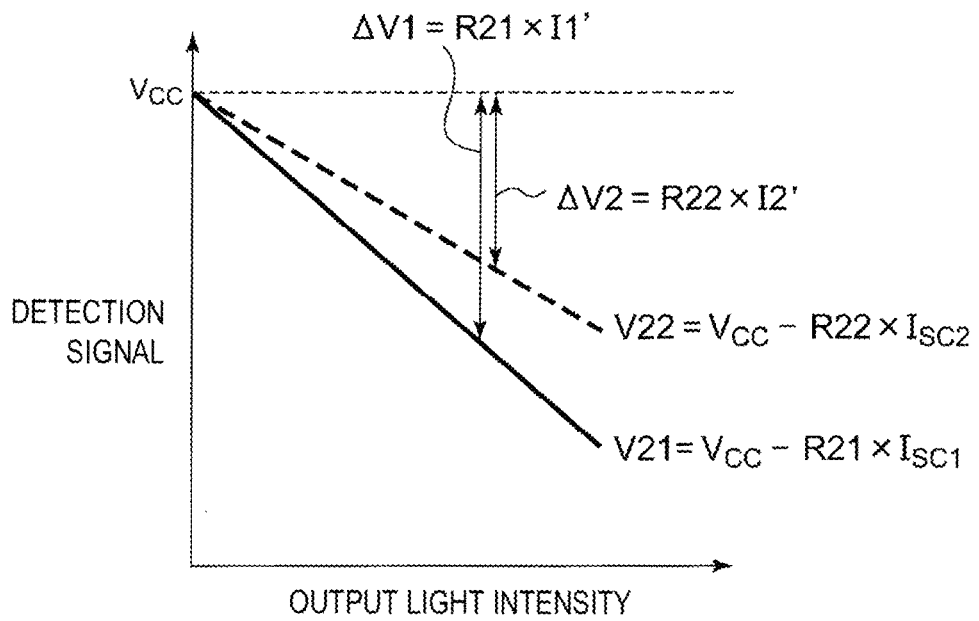
FIG. 7B shows the relation among the output light intensity, the first detection signal and the second detection signal when the fluorescent substance is abnormal.

FIG. 7A shows a relation among the output light intensity, the first detection signal V21 and the second detection signal V22 when the fluorescent substance 14 is normal, and FIG. 7B shows the relation among the output light intensity, the first detection signal V21 and the second detection signal V22 when the fluorescent substance 14 is abnormal. As described above, the resistance values of the resistances R21, R22 are determined to satisfy the relation equations (1) and (2). Therefore, when the fluorescent substance is normal, V21 becomes larger than V22, and when the fluorescent substance is abnormal, V22 becomes larger than V21. A voltage comparator CMP21 of FIG. 6 sets the abnormality detection signal S1 to the low level (negate) when V21>V22, i.e., when the fluorescent substance is normal, and sets the abnormality detection signal S1 to the high level (assert) when V21<V22.

According to the configuration example, it is possible to achieve the same effects as the abnormality detector 30 of FIG. 5.

Third Configuration Example

Returning to FIGS. 4A and 4B, according to the first configuration example of FIG. 5, since the detection currents $I_{SC1}$, $I_{SC2}$ are small in a region where the output light intensity is low, the first detection signal V21 and the second detection signal V22 approximate. Therefore, when the noise, the variation of elements, offset voltages of the operational amplifier and the voltage comparator, and the like (hereinafter, referred to as error factors) are non-negligibly large, the magnitude relation of the first detection signal V21 and the second detection signal V22 are reversed in the range where the output light intensity is low, so that an abnormality may be falsely detected or an abnormality cannot be detected even though an abnormality occurs. As can be seen from FIGS. 7A and 7B, similar problem may be also caused in the second configuration example of FIG. 6.

Therefore, according to a third configuration example, the determination unit 40 is configured to offset at least one of the first detection signal V21 and the second detection signal V22 in a direction of separating away from each other and to determine whether an abnormality occurs based on the detection signals V21, V22 after the offset.

Figure 8A:
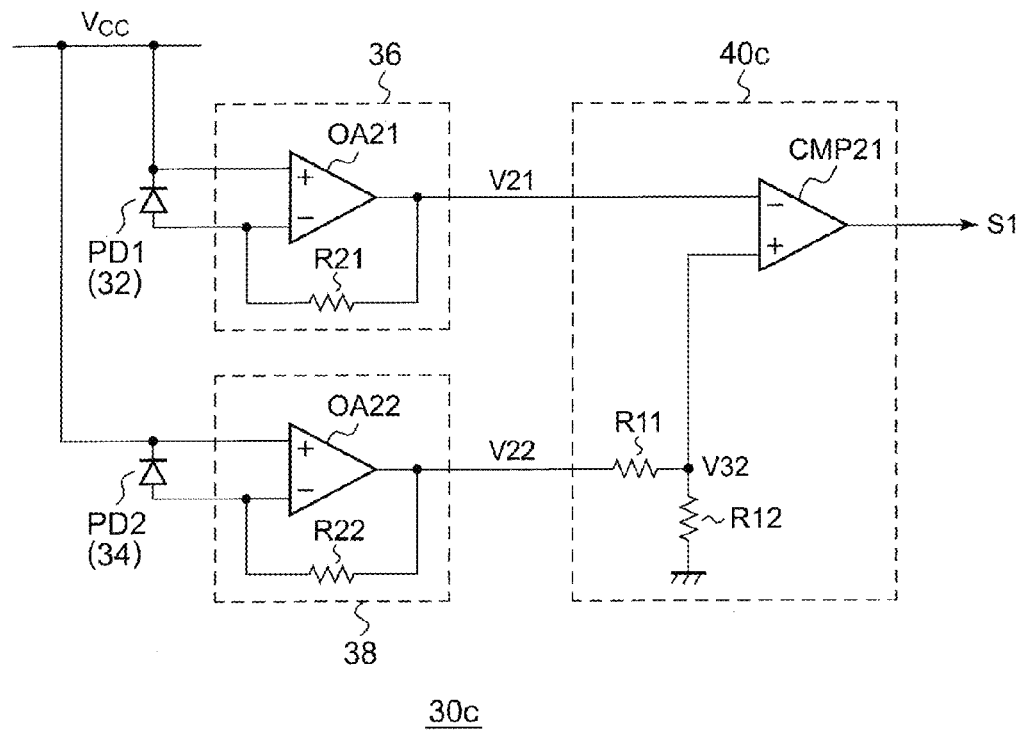
FIG. 8A is a circuit diagram of an abnormality detector according to a third configuration example.

FIG. 8A is a circuit diagram of an abnormality detector 30c according to the third configuration example. A determination unit 40c includes voltage-dividing circuits R11, R12 in addition to the voltage comparator CMP21. The voltage-dividing circuits R11, R12 are configured to voltage-divide the second detection signal V22. The voltage comparator CMP21 is configured to compare a second detection signal V32 after the voltage division and the first detection signal V21 and to generate the abnormality detection signal S1.

Figure 9A:
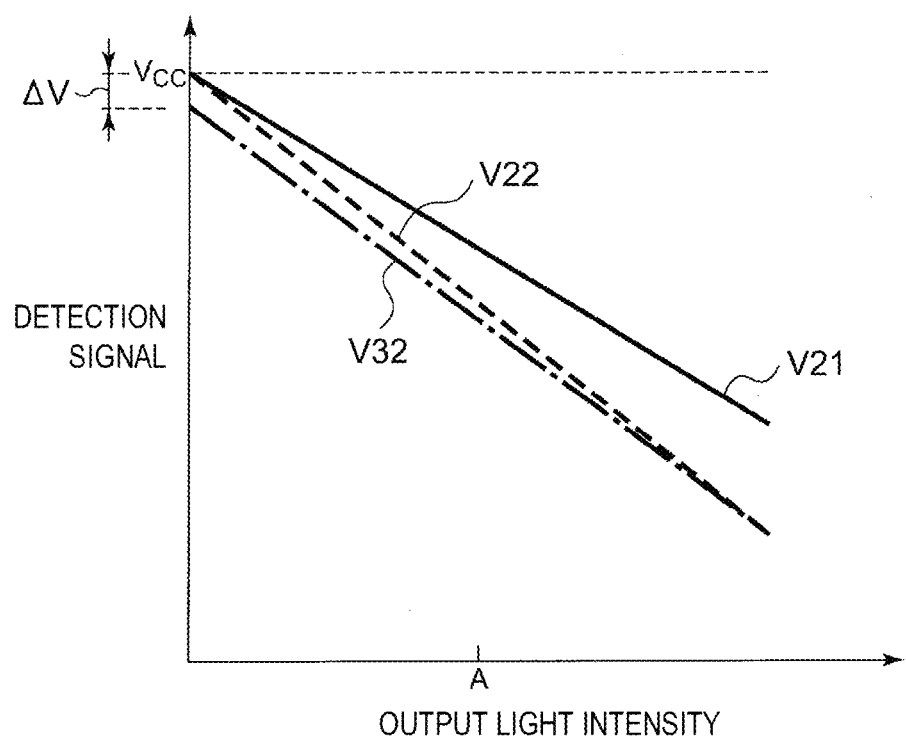
FIG. 9A shows a relation among the output light intensity, the first detection signal and the second detection signal in the abnormality detector of FIG. 8A when the fluorescent substance is normal.

FIG. 9A shows a relation among the output light intensity, the first detection signal V21 and the second detection signal V22 in the abnormality detector 30c of FIG. 8A when the fluorescent substance 14 is normal. In the abnormality detector 30c, the second detection signal V32 after the voltage division is expressed by an equation (7).

$$V32 = R12/(R11 + R12) \times V22 \qquad (7)$$
$$= R12/(R11 + R12) \times Vcc - R12/(R11 + R12) \times R22 \times I_{SC2}$$

That is, a y-intercept of the second detection signal V32 in FIG. 9A is offset in the direction of separating from the first detection signal V21. An offset width ΔV is $V_{CC} \times R11/(R11+R12)$ and can be set by the resistances R11, R12. For example, it is assumed that the offset voltage of the voltage comparator CMP21 is dominant as the error factor. In this case, the offset width ΔV is preferably slightly greater than the offset voltage of the voltage comparator CMP21 (for example, 20 mV).

In this way, according to the third configuration example, it is possible to increase the detection precision in the range where the output light intensity is low. Particularly, in FIG. 8A, since the two resistances R11, R12 of the voltage-dividing circuit have only to be inserted, it is possible to increase the detection precision at low costs and with a small area.

Also, as described above, an absolute value of a gradient of the second detection signal V32 after the voltage division is reduced by the voltage-dividing circuits R11, R12, as compared to a configuration where the voltage-dividing circuit is not provided. Therefore, in a region A of steady lighting where the output light intensity is somewhat high, the influence of the offset width ΔV by the voltage-dividing circuit is sufficiently reduced, as compared to the region where the output light intensity is low, and the influence on the detection value can be negligible.

When the voltage-dividing circuits R11, R12 are introduced and the resistance value of the second resistance R22 is optimized, the gradient of the second detection signal V32 and the offset width ΔV can be independently and arbitrarily set.

Figure 8B:
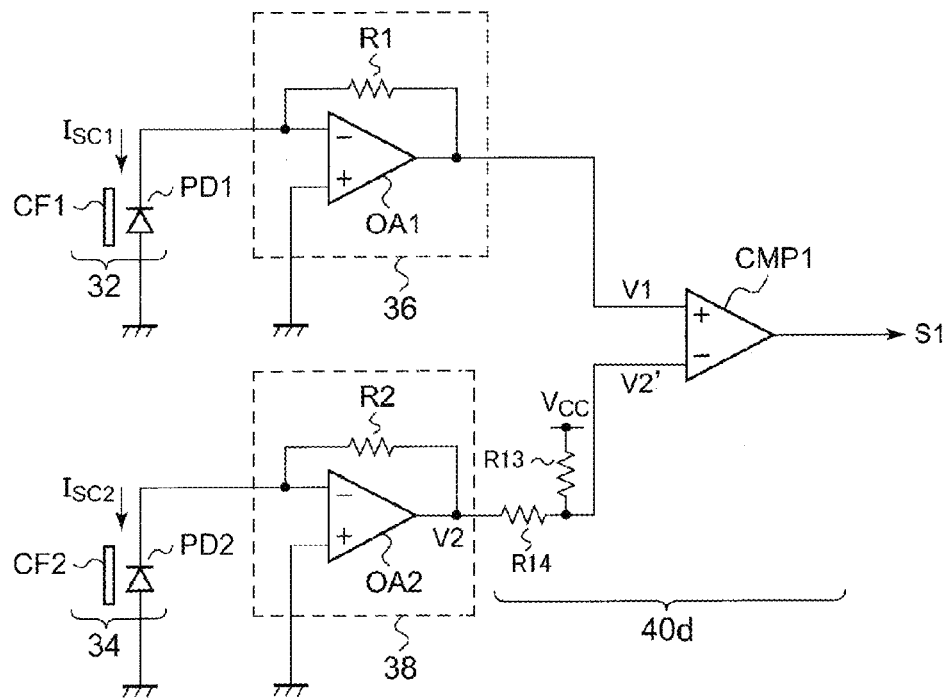
FIG. 8B is a circuit diagram of an abnormality detector according to a fourth configuration example.

FIG. 8B is a circuit diagram of an abnormality detector 30d according to a fourth configuration example. A determination unit 40d includes voltage-dividing circuits R13, R14 in addition to the voltage comparator CMP1. The voltage-dividing circuits R13, R14 are configured to voltage-divide the second detection signal V2 and the power supply voltage $V_{CC}$. The voltage comparator CMP1 is configured to compare a second detection signal V2' after the voltage division and the first detection signal V1 and to generate the abnormality detection signal S1.

Figure 9B:
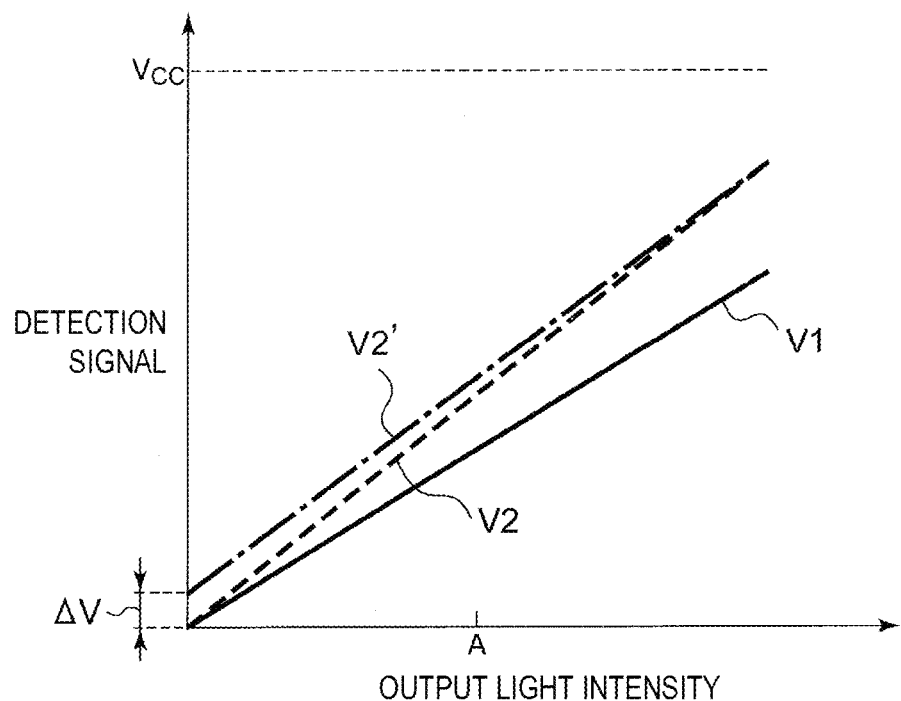
FIG. 9B shows a relation among the output light intensity, the first detection signal and the second detection signal in the abnormality detector of FIG. 8B when the fluorescent substance is normal.

FIG. 9B shows a relation among the output light intensity, the first detection signal V1 and the second detection signal V2' in the abnormality detector 30d of FIG. 8B when the fluorescent substance 14 is normal. In the abnormality detector 30d, the second detection signal V2' after the voltage division is expressed by an equation (8).

$$V2' = (R13 \cdot V2 + R14 \cdot Vcc)/(R13 + R14) \qquad (8)$$

$$= R13 \cdot R2 \times I_{SC2} + R14 \cdot Vcc)/(R13 + R14)$$

That is, a y-intercept of the second detection signal V2' in FIG. 9B is offset in the direction of separating from the first detection signal V1. The offset width ΔV is $R14 \cdot V_{CC}/(R13+R14)$ and can be set by the resistances R13, R14. Also in the fourth configuration example, it is possible to achieve the same effects as the third configuration example.

Subsequently, modified illustrative embodiments of the first illustrative embodiment are described.

First Modified Illustrative Embodiment

In the illustrative embodiment, the determination unit 40 is configured by the voltage comparator CMP1. However, the present invention is not limited thereto. For example, the determination unit 40 may include an A/D converter configured to convert the first detection signal V1 and the second detection signal V2 into digital values D1, D2, and may be configured to determine whether an abnormality occurs by performing digital signal processing for the digital values D1, D2.

Second Modified Illustrative Embodiment

The method of introducing the offset width ΔV is not limited to the voltage-dividing circuits R11, R12. For example, the comparator CMP1 may be configured to adjust an input offset voltage, and at least one of the first detection signal V1 and the second detection signal V2 may be offset. In this case, it is possible to prevent the false detection due to the error factors such as the noise.

Third Modified Illustrative Embodiment

In the abnormality detector 30a of FIG. 5, it is also effective to offset at least one of the first detection signal V1 and the second detection signal V2. Specifically, the second detection signal V2 of FIG. 4A may be offset in a positive direction. In order to realize this, the fixed voltage corresponding to the offset width ΔV may be applied to the non-inverting input terminal (+) of the first operational amplifier OA1.

Fourth Modified Illustrative Embodiment

Figure 10:
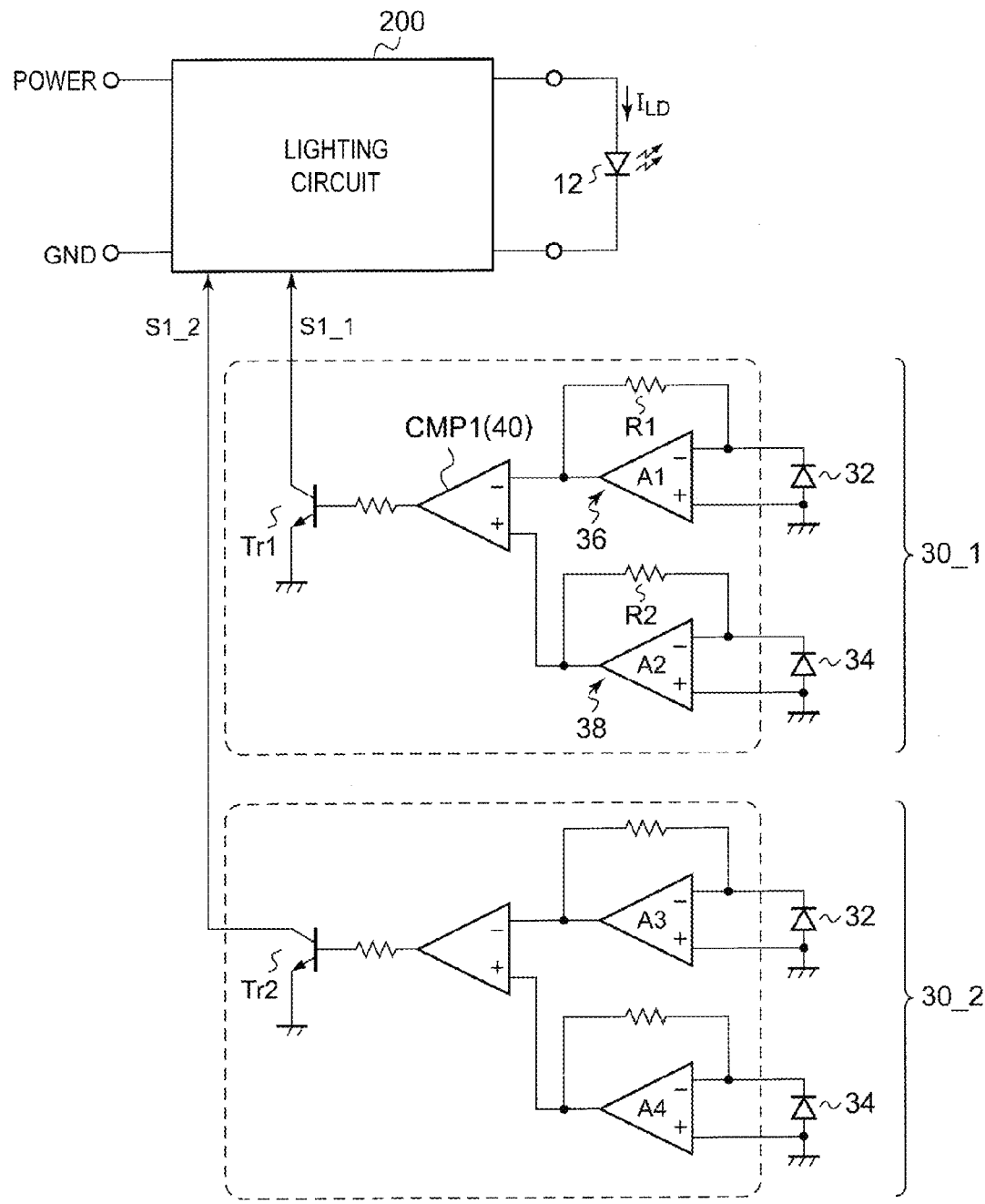
FIG. 10 is a block diagram of a vehicle lamp device according to a fourth modified illustrative embodiment.

FIG. 10 is a block diagram of a vehicle lamp device 1b according to a fourth modified illustrative embodiment. The vehicle lamp device 1b includes a plurality of (two, in this illustrative embodiment) abnormality detectors 30. As the abnormality detector 30, any one described in the first illustrative embodiment and the modified illustrative embodiments thereof may be used. The two abnormality detectors 30 may have the same configuration or the abnormality detectors having different configurations may be combined.

The lighting circuit 200 is input with abnormality detection signals S1_1, S1_2, which are the outputs of the respective abnormality detectors, through separate routes. The lighting circuit 200 is configured to function as a failure latch for the plurality of abnormality detection signals S1_1, S1_2, and to execute protection processing when any one indicates an abnormality. As described above, in the protection processing, the lighting circuit 200 may stop the supply of the driving current $I_{LD}$ such that the laser diode 12 is turned off when any one abnormality detection signal S1 is asserted.

Similarly, according to the fourth modified illustrative embodiment, the plurality of abnormality detectors 30 are provided, and the plurality of abnormality detection signals S1 obtained therefrom is applied to the failure latch for protection of the lighting circuit 200 through the separate routes. Thereby, even when a failure occurs in the abnormality detector 30 of any system, since it is possible to detect the abnormality in the separate system, it is possible to increase the robustness.

Meanwhile, in the fourth modified illustrative embodiment, one terminal for failure latch of the lighting circuit 200 may be configured and collectors of transistors Tr1, Tr2 provided at output terminals of the plurality of abnormality detectors 30_1, 30_2 may be commonly connected to the terminal for failure latch. In this case, the transistors Tr1, Tr2 configure an OR circuit, and the protection processing is performed when at least one of the abnormality detectors 30 detects the abnormality.

Subsequently, a package of the first photo diode PD1 and the second photo diode PD2 for abnormality detection is described.

When the photo diode is used for vehicle, a CAN package is adopted so as to secure the long-term reliability under severe environments where the photo diode is exposed to the high temperature and humidity and the thermal shock. Here, when the two photo diodes are accommodated in one package, the cathodes are commonly connected and are electrically connected to a metallic case.

Here, when it is desired to use a pair of photo diodes of which cathodes are common and which is accommodated in the CAN package, it is not possible to adopt the non-inverting current-voltage conversion circuits 36, 38 of FIG. 5, and it is necessary to adopt the inverting current-voltage conversion circuit 36, 38 shown in FIGS. 6 and 8A. In this case, when a pair of photo diodes of the CAN package is used for the abnormality detectors 30b, 30c of FIGS. 6 and 8A, since the potential of the cathode becomes the power supply voltage $V_{CC}$, a potential of the metallic case also becomes the power supply voltage $V_{CC}$. Here, a metallic structure in the lamp device is grounded in many cases as the measures against the electromagnetic noise. Therefore, when the metallic case is contacted to the surrounding metallic structure, a short occurs between the power supply and the ground, so that the photo diodes cannot operate and the other circuit blocks sharing the power supply voltage $V_{CC}$ cannot also operate.

Figure 11B:
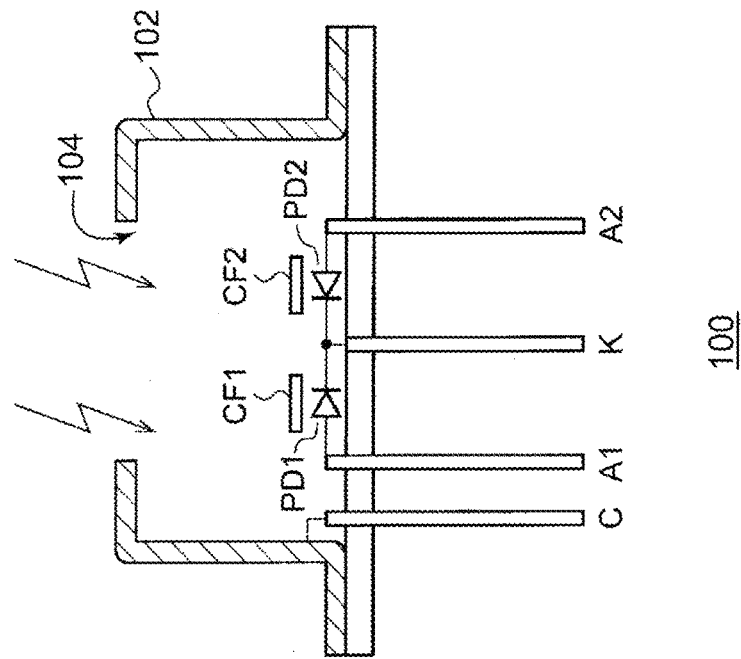
FIG. 11B is a pictorial sectional view thereof.
Figure 11A:
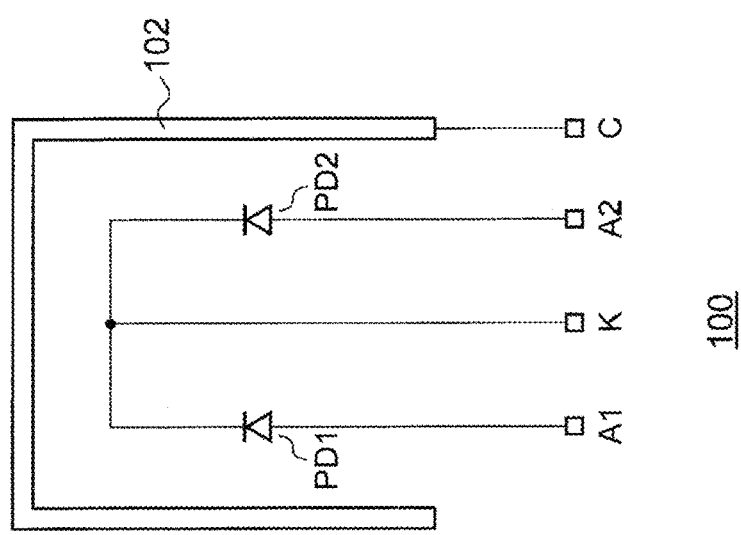
FIG. 11A is an equivalent circuit diagram of a photo diode module including a pair of photo diodes.

Therefore, in the abnormality detectors 30b, 30c of FIGS. 6 and 8A, the photo diodes PD1, PD2 are accommodated in a photo diode module 100 having the following structure. FIG. 11A is an equivalent circuit diagram of the photo diode module 100 including the pair of photo diodes PD1, PD2, and FIG. 11B is a pictorial sectional view thereof. The photo diode module 100 includes anode terminals A1, A2, a cathode terminal K, two photo diodes PD1, PD2 and a metallic case 102. The metallic case 102 is electrically insulated from the cathode terminal K. The metallic case is formed with an opening 104 on its upper surface, and the light can be incident to the photo diodes PD1, PD2. A light receiving part of each of the photo diodes PD1, PD2 may be covered with a color filter.

Here, in a utility of the abnormality detector 30, since the current flowing through the photo diodes PD1, PD2 is very small such as μA order and the input impedance of the current-voltage conversion circuit is very high, it can be said that the noise resistance is low. Therefore, the photo diode module 100 is preferably provided with a case terminal C electrically connected to the metallic case 102. In this case, when the terminal C is grounded, the metallic case 102 functions as a shield, so that it is possible to increase the resistance against the electromagnetic noise.

Second Illustrative Embodiment

Figure 12:
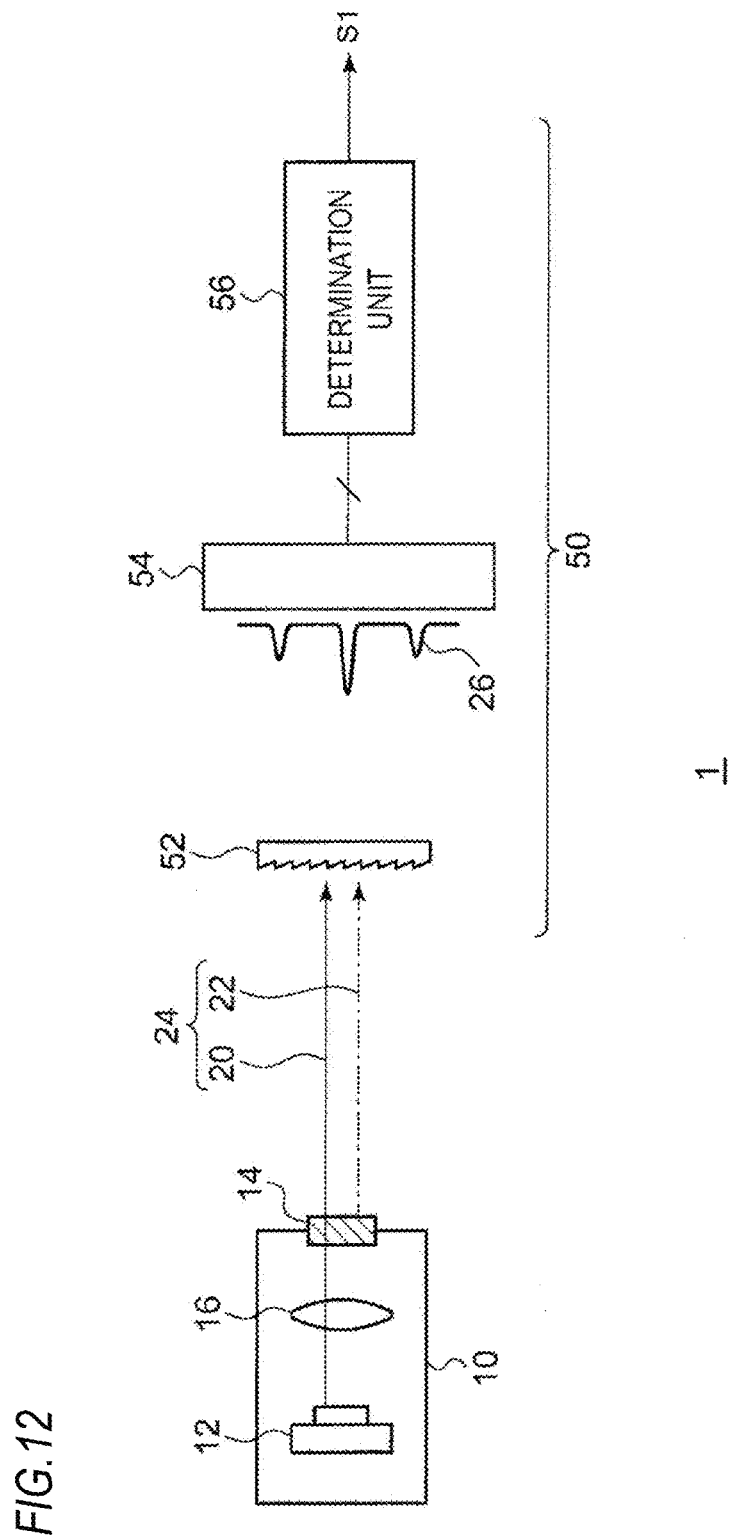
FIG. 12 is a block diagram of a vehicle lamp device having an abnormality detector according to a second illustrative embodiment.

FIG. 12 is a block diagram of a vehicle lamp device 1 having an abnormality detector 50 according to a second illustrative embodiment. The vehicle lamp device 1 includes the light source 10 and the abnormality detector 50 configured to detect an abnormality of the light source 10. The light source 10 is similar to that in the first illustrative embodiment and is configured to generate the white output light 24 including the spectra of the excitation light 20 and the fluorescent light 22.

The abnormality detector 50 is configured to receive a part of the output light 24 and to determine whether an abnormality occurs in the light source 10, more specifically, whether an abnormality occurs in the fluorescent substance 14. The abnormality of the fluorescent substance 14 may be, for example, breaking, removal, aging deterioration and the like of the fluorescent substance 14, but not limited to those.

The abnormality detector 50 includes a diffraction element 52, a light detector 54 and a determination unit 56.

The diffraction element 52 is configured to diffract the output light 24 of the light source 10. For example, the diffraction element 52 may be a transmission type or a reflection type diffraction grating. The light detector 54 is configured to detect a diffracted light 26 of the diffraction element 52. The determination unit 56 is configured to determine whether an abnormality occurs based on a detection result of the light detector 54.

The above is the basic configuration of the abnormality detector 50. Subsequently, an operation principle thereof is described.

Figure 13B:
FIG. 13B shows a diffracted light when the fluorescent substance is abnormal.
Figure 13A:
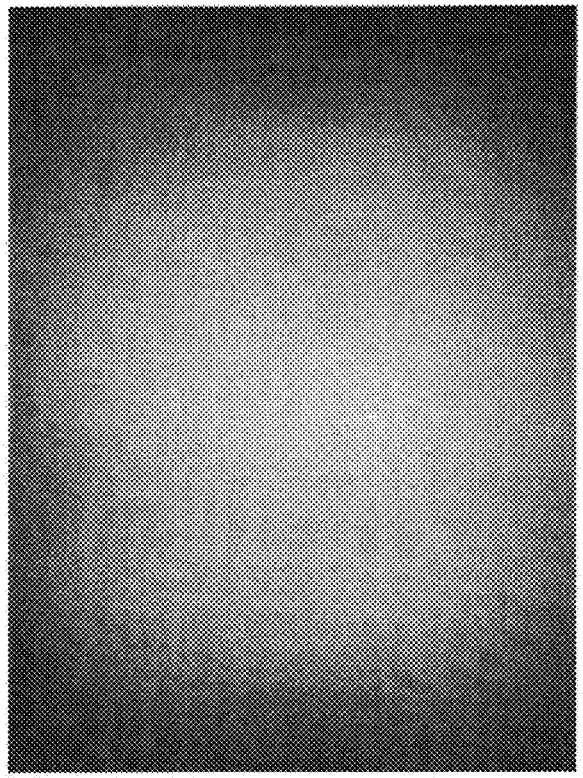
FIG. 13A shows a diffracted light when the fluorescent substance is normal.

FIG. 13A shows the diffracted light when the fluorescent substance is normal, and FIG. 13B shows the diffracted light when the fluorescent substance is abnormal.

When the fluorescent substance 14 is normal, the excitation light 20 is scattered by the fluorescent substance 14. Therefore, the excitation light 20 incident to the diffraction element 52 is lowered in coherency, so that a substantial interference fringe is not observed in the diffracted light 26 obtained by the diffraction element 52 (FIG. 13A). On the other hand, when the fluorescent substance 14 is abnormal, the excitation light 20 is not scattered and is coherently incident to the diffraction element 52. Therefore, a substantial interference fringe is observed in the diffracted light 26 obtained by the diffraction element 52 (FIG. 13B).

Therefore, according to the abnormality detector 50, it is possible to determine whether the fluorescent substance 14 is abnormal based on the diffracted light 26 obtained by the diffraction element 52, more specifically, depending on whether the substantial diffraction pattern (interference fringe) is observed.

The scope of the present invention includes various circuits which can be perceived from the block diagram of FIG. 12. In the below, specific configuration examples are described.

First Configuration Example

Figure 14:
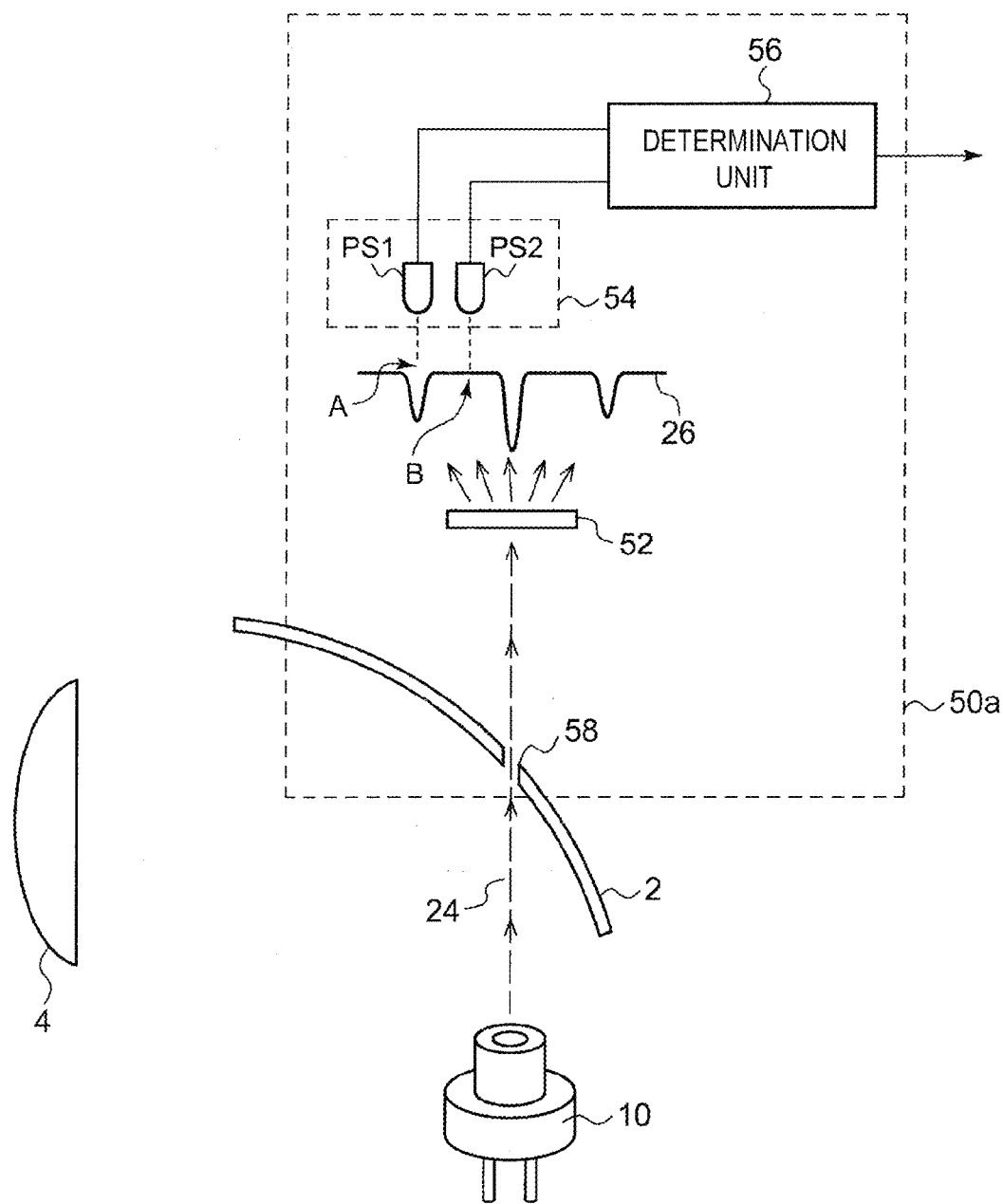
FIG. 14 illustrates a vehicle lamp device including an abnormality detector according to a first configuration example.

FIG. 14 illustrates a vehicle lamp device 1a including an abnormality detector 50a according to a first configuration example. The vehicle lamp device 1a includes the light source 10, a reflector 2 configured to reflect the emission light 24 of the light source 10 and a lens 4 configured to receive the emission light 24 reflected on the reflector 2 and to emit the same to the front of the lamp device. The reflector 2 is formed with a pinhole. The reflector 2 is provided on its backside with the diffraction element 52, and a part of the light passing through the pinhole 58 of the emission light 24 reaches the diffraction element 52. A size (opening area) of the pinhole 58 is not particularly limited.

The light detector 54 is configured to detect the light intensities of two points, i.e., a first position A at which a pattern of the diffracted light 26 has a peak when the fluorescent substance 14 is normal and a second position B at which there is no peak when the fluorescent substance 14 is normal. For example, the light detector 54 includes two photo sensors PS1, PS2 provided at the two positions A, B. The light detector 54 is configured to be sensitive to the blue light, which is the excitation light 20, and is preferably insensitive to the yellow light, which is the fluorescent light.

The determination unit 56 is configured to determine whether an abnormality occurs based on the light intensities at the two points. More specifically, the determination unit 56 may determine that the fluorescent substance 14 is abnormal when a difference of outputs of the two photo sensors PS1, PS2 exceeds a predetermined threshold.

Alternatively, the determination unit 56 may be configured to determine whether an abnormality occurs based on a ratio of the light intensities, instead of the difference of the light intensities at the points A, B. In this case, it is possible to determine whether an abnormality occurs irrespective of the output light intensity of the light source 10. Alternatively, the determination unit 56 may be configured to determine whether an abnormality occurs by a combination of the difference and the ratio.

Instead of the configuration where the reflector 2 is formed with the pinhole 58, a part of the reflector 2 may be made to have a lower reflectivity so that the output light 24 of the light source 10 can penetrate therethrough.

Figure 15A:
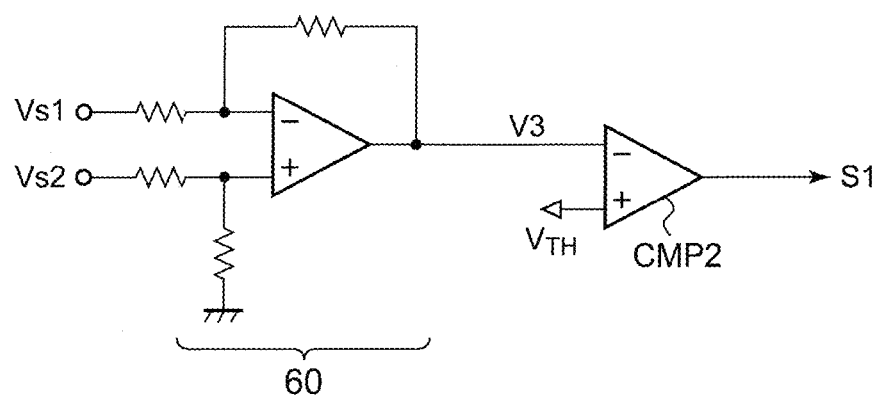
FIGS. 15A and 15B are circuit diagrams showing specific configuration examples of a determination unit.
Figure 15B:
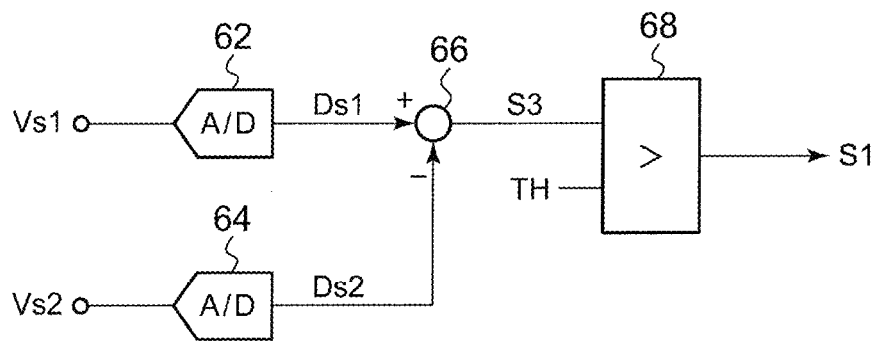

FIGS. 15A and 15B are circuit diagrams showing specific configuration examples of the determination unit 56.

The determination unit 56 of FIG. 15A includes a differential calculating unit 60 and a voltage comparator CMP2. The differential calculating unit 60 is configured to receive a detection signal Vs1 from the photo sensor PS1 and a detection signal Vs2 from the photo sensor PS2 and to amplify a difference thereof. The configuration of the differential arithmetic unit 60 is not particularly limited and a known configuration may be used. The voltage comparator CMP2 is configured to compare an output voltage V3 of the differential calculating unit 60 and a predetermined threshold voltage $V_{TH}$. The output (abnormality detection signal S1) of the voltage comparator CMP2 is negated when the difference of the outputs of the two photo sensors is smaller than the threshold, and is asserted when the difference is larger than the threshold. In this configuration example, a negative logic system is adopted, and a low level is allotted to the assert and a high level is allotted to the negate.

The determination unit 56 may be configured by a digital circuit. The determination unit 56 of FIG. 15B includes A/D converters 62, 64, a subtractor 66 and a comparator 68. The A/D converters 62, 64 are configured to convert the detection signals Vs1, Vs2 of the photo sensors PS1, PS2 into digital signals Ds1, Ds2. The A/D converter 64 is configured to calculate a differential signal S3 of the digital signals Ds1, Ds2. The comparator 68 is configured to determine whether an abnormality occurs by comparing the differential signal S3 and the threshold TH.

Second Configuration Example

Figure 16:
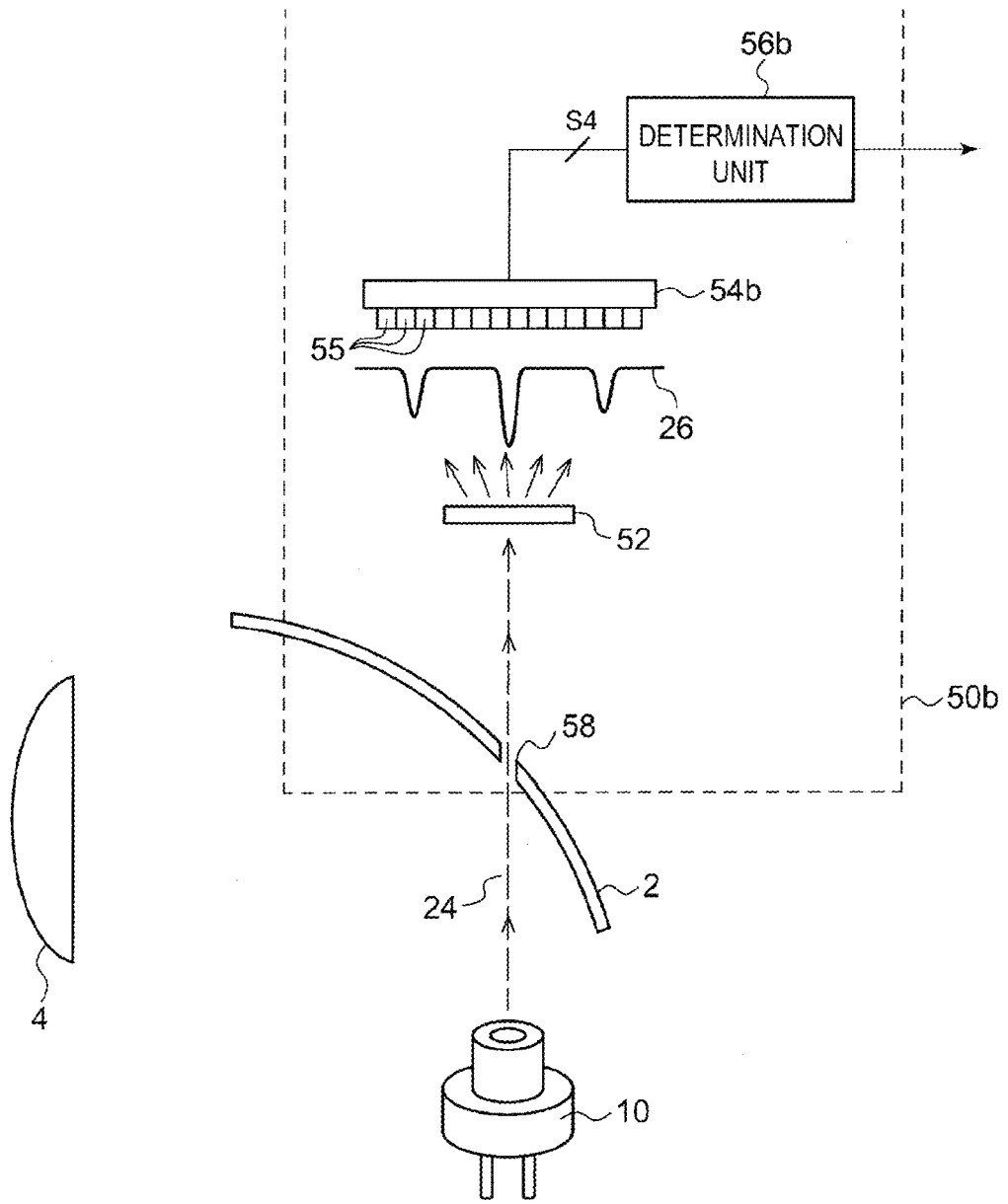
FIG. 16 is a circuit diagram showing an abnormality detector according to a second configuration example.

FIG. 16 is a circuit diagram showing an abnormality detector 50b according to a second configuration example. A light detector 54b includes a plurality of pixels 55 configured to receive the diffracted light 26. The light detector 54b can use a CCD or CMOS sensor and may be combined with a color filter. The light detector 54b may be a line sensor including a plurality of pixels arranged in one dimensional shape or may be a matrix array sensor including a plurality of pixels arranged in a matrix shape.

The determination unit 56b is configured to determine whether an abnormality occurs based on a pattern of the diffracted light 26 measured by the plurality of pixels 55. In the below, some determination methods by the abnormality detector 50b are described.

For example, pixels, which correspond to the points A, B of FIG. 14, of the plurality of pixels 55 may be used as the photo sensors PS1, PS2 of FIG. 14. In this case, the processing of the determination unit 56b is as described above.

Alternatively, there may be employed a method which includes acquiring a pattern of the diffracted light 26 by using all or some of the plurality of pixels 55, comparing the acquired pattern and a predetermined diffraction pattern, detecting whether an interference fringe exists by determining how the patterns are matched, and determining whether an abnormality occurs.

Figure 17A:
FIG. 17A shows an output of a light detector and differential data thereof when the fluorescent substance is abnormal.
Figure 17B:
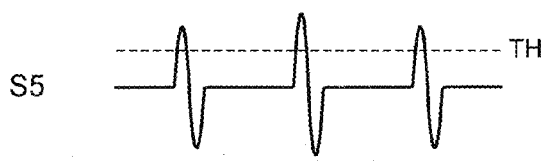
FIG. 17B shows an output of the light detector and differential data thereof when the fluorescent substance is normal.

Alternatively, the determination unit 56 may be configured to determine whether an abnormality occurs by executing arithmetic processing for data of the diffracted light 26 measured by the light detector 54b. FIG. 17A shows an output S4 of the light detector 54b and differential data S5 thereof when the fluorescent substance 14 is abnormal, and FIG. 17B shows the output S4 of the light detector 54b and differential data S5 thereof when the fluorescent substance 14 is normal.

A configuration of differentiating the output S4 of the light detector 54b is equivalent to a configuration of spatially differentiating data measured by the plurality of pixels 55, and an edge of the interference fringe can be detected by the differential processing. Also, it is possible to determine whether the fluorescent substance 14 is abnormal by comparing the differential data S5 and the predetermined threshold TH to determine whether the substantial interference fringe occurs. In the meantime, the threshold TH may be provided in a negative direction. In this case, it is possible to detect an edge opposite to the interference fringe. Alternatively, the threshold TH may be set at both positive and negative sides.

Figure 18:
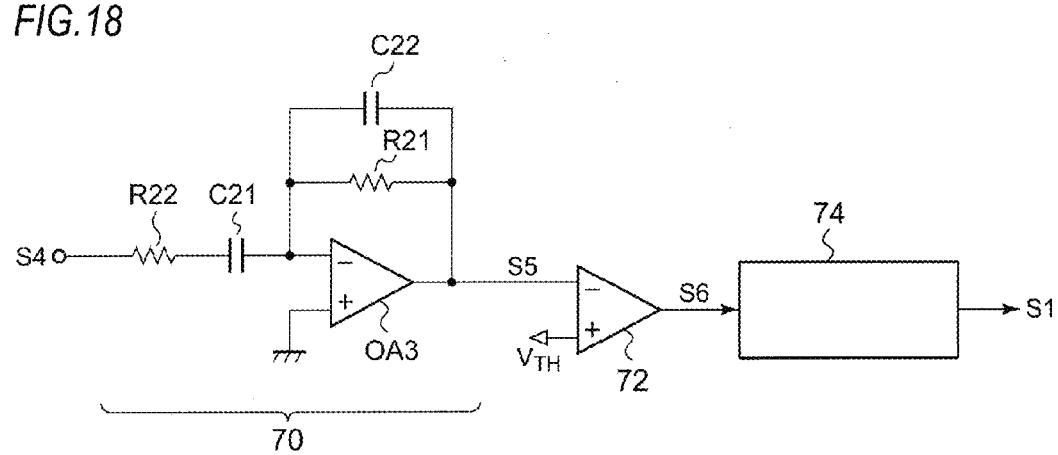
FIG. 18 is a circuit diagram showing a configuration example of the determination unit.

FIG. 18 is a circuit diagram showing a configuration example of the determination unit 56b. The determination unit 56b includes a differentiator 70 configured to spatially differentiate the data S4, which indicates the diffracted light 26. The data S4 obtained from the plurality of pixels 55 of the light detector 54b may be sequentially read from an end. At this time, the spatial differentiation is equivalent to a configuration of temporally differentiating the data S4 sequentially read from the plurality of pixels 55. Therefore, the differentiator 70 may be configured by a differential amplifier (high-pass filter) configured to differentiate the analog data signal S4. The differential amplifier (high-pass filter) mainly includes a resistance R21, a capacitor C21 and an operational amplifier OA3.

The voltage comparator 72 is configured to compare an output signal S5 of the differentiator 70 and the threshold $V_{TH}$, and outputs a low level when S5>$V_{TH}$, and a high level when S5<$V_{TH}$. A subsequent stage of the voltage comparator 72 may be provided with a final determination circuit 74 including a filter, a timer and the like. The final determination circuit 74 determines that the fluorescent substance 14 is abnormal and asserts (high level) the abnormality detection signal S1 when the output of the voltage comparator 72 keeps the low level for a predetermined determination time period.

When the signal S4 from the light detector 54b includes many noises, the noise is amplified by the differentiator 70 so that the S/N ratio may be lowered. Therefore, the differentiator 70 may be added with a resistance R22 (R11>R22) and a capacitor C22 (C21>C22) configured to form a weak integrator (low-pass filter) together with the operational amplifier OA3. Thereby, it is possible to remove the noise and to thus increase the S/N ratio.

In FIG. 18, the determination unit 56b of the analog circuit is shown. However, it is understood that one skilled in the art can implement processing equivalent thereto by a digital circuit. Specifically, there may be used a method which includes converting the analog detection signal S4 from the light detector 54b into a digital value by the A/D converter, differentiating the digital value and comparing the same and a threshold to determine whether an abnormality occurs.

Figure 19:
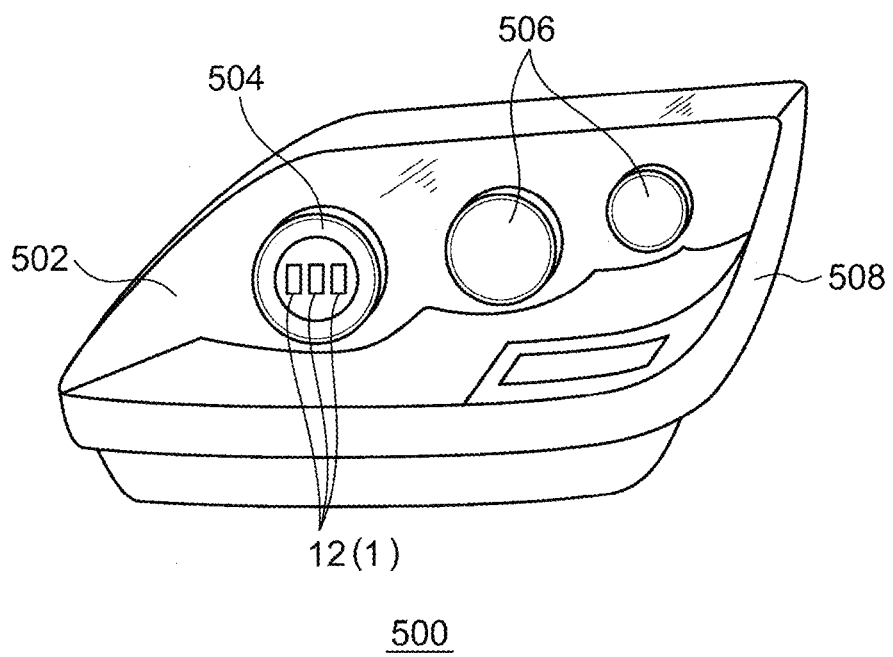
FIG. 19 is a perspective view of a lamp unit having a vehicle lamp device according to an illustrative embodiment.

Finally, a utility of the vehicle lamp device 1 is described. FIG. 19 is a perspective view of a lamp unit (lamp assembly) 500 having the vehicle lamp device 1 according to the illustrative embodiments. The lamp unit 500 includes a transparent cover 502, a high beam unit 504, a low beam unit 506 and a housing 508. The vehicle lamp device 1 may be used for the high beam unit 504, for example. The vehicle lamp device 1 includes the one or more light sources 10. Instead of the high beam unit 504 or in addition to the high beam unit 504, the vehicle lamp device 1 may be used for the low beam unit 506.

Although the present invention has been described using the specific expressions based on the illustrative embodiments, the illustrative embodiments are provided only to describe the principle and application of the present invention, and various modified embodiments and changes in the arrangement can be made without departing from the spirit of the present invention defined in the claims.

What is claimed is:

1. An abnormality detector for a light source which includes a laser diode configured to emit an excitation light and a fluorescent substance configured to be excited by the excitation light to generate a fluorescent light, and which is configured to generate a white output light having spectra of the excitation light and the fluorescent light, the abnormality detector comprising:
   a first photo sensor which is sensitive to a wavelength of the excitation light and substantially insensitive to a wavelength of the fluorescent light and which is configured to receive a part of the output light to generate a first current in accordance with an amount of the received light;
   a second photo sensor which is sensitive to the wavelength of the fluorescent light and substantially insensitive to the wavelength of the excitation light and which is configured to receive a part of the output light to generate a second current in accordance with an amount of the received light;

a first current-voltage conversion circuit which includes a first resistance provided on a path of the first current and which is configured to output a first detection signal corresponding to a voltage drop of the first resistance;

a second current-voltage conversion circuit which includes a second resistance provided on a path of the second current and which is configured to output a second detection signal corresponding to a voltage drop of the second resistance; and a determination unit which is configured to determine whether an abnormality occurs based on the first detection signal and the second detection signal.

2. The abnormality detector according to claim 1,
wherein in a case where the first current is denoted as I1 and the second current is denoted as I2 when the fluorescent substance is normal, and the first current is denoted as I1' and the second current is denoted as I2' when the fluorescent substance is abnormal, a resistance value R1 of the first resistance and a resistance value R2 of the second resistance satisfy the following relation equations:

$$R1 \times I1 < R2 \times I2 \quad (1); \text{ and}$$

$$R1 \times I1' > R2 \times I2' \quad (2).$$

3. The abnormality detector according to claim
wherein the determination unit is configured to determine that an abnormality occurs when a magnitude relation of the first detection signal and the second detection signal is reversed.

4. The abnormality detector according to claim 3,
wherein the determination unit includes a voltage comparator.

5. The abnormality detector according to claim 1,
wherein the first current-voltage conversion circuit includes:
a first operational amplifier having an inverting input terminal to which the first photo sensor is connected and a non-inverting input terminal to which a fixed voltage is applied; and
the first resistance provided between the inverting input terminal and an output terminal of the first operational amplifier, and
wherein the second current-voltage conversion circuit includes:
a second operational amplifier having an inverting input terminal to which the second photo sensor is connected and a non-inverting input terminal to which a fixed voltage is applied; and
the second resistance provided between the inverting input terminal and an output terminal of the second operational amplifier.

6. The abnormality detector according to claim 5,
wherein the first photo sensor includes a first photo diode, and the second photo sensor includes a second photo diode,
wherein a cathode of the first photo diode is connected to the inverting input terminal of the first operational amplifier and a fixed voltage is applied to an anode of the first photo diode, and
wherein a cathode of the second photo diode is connected to the inverting input terminal of the second operational amplifier and a fixed voltage is applied to an anode of the second photo diode.

7. The abnormality detector according to claim 5,
wherein the first photo sensor includes a first photo diode, and the second photo sensor includes a second photo diode,
wherein the inverting input terminal of the first operational amplifier is connected with an anode of the first photo diode, and the non-inverting input terminal of the first operational amplifier is connected with a cathode of the first photo diode and is applied with a fixed voltage, and
wherein the inverting input terminal of the second operational amplifier is connected with an anode of the second photo diode, and the non-inverting input terminal of the second operational amplifier is connected with a cathode of the second photo diode and is applied with a fixed voltage.

8. The abnormality detector according to claim 1,
wherein the determination unit is configured to offset at least one of the first detection signal and the second detection signal in a direction of separating from each other.

9. The abnormality detector according to claim 7,
wherein the determination unit includes a voltage-dividing circuit configured to voltage-divide the second detection signal.

10. A vehicle lamp device comprising:
the abnormality detector according to claim 1 which is configured to detect an abnormality of the light source;
the light source; and
a lighting circuit which is configured to drive the light source and to execute predetermined protection processing when the abnormality detector detects an abnormality of the light source.

11. The vehicle lamp device according to claim 10,
wherein a plurality of the abnormality detectors are provided, and
wherein the lighting circuit executes the protection processing when at least one the abnormality detectors detects an abnormality.

12. An abnormality detector for a light source which includes a laser diode configured to emit an excitation light and a fluorescent substance configured to be excited by the excitation light to generate a fluorescent light, and which is configured to generate a white output light having spectra of the excitation light and the fluorescent light, the abnormality detector comprising:
a diffraction element which is configured to diffract the output light of the light source;
a light detector which is configured to detect a diffracted light by the diffraction element; and
a determination unit which is configured to determine whether an abnormality occurs based on a detection result of the light detector,
wherein the fluorescent substance is disposed between the laser diode and the diffraction element.

13. An abnormality detector for a light source which includes a laser diode configured to emit an excitation light and a fluorescent substance configured to be excited by the excitation light to generate a fluorescent light, and which is configured to generate a white output light having spectra of the excitation light and the fluorescent light, the abnormality detector comprising:
a diffraction element which is configured to diffract the output light of the light source;
a light detector which is configured to detect a diffracted light by the diffraction element;

a determination unit which is configured to determine whether an abnormality occurs based on a detection result of the light detector, wherein the light detector is configured to detect light intensities of two positions including a first position at which a pattern of the diffracted light has a peak when the fluorescent substance is normal and a second position at which there is no peak when the fluorescent substance is normal, and wherein the determination unit is configured to determine whether an abnormality occurs based on the light intensities of the two positions.

14. The abnormality detector according to claim 13, wherein the light detector includes two photo sensors provided at the two positions, and wherein the determination unit is configured to determine that an abnormality occurs when a difference of outputs of the two photo sensors exceeds a predetermined threshold.

15. The abnormality detector according to claim 12, wherein the light detector includes a plurality of pixels configured to receive the diffracted light, and wherein the determination unit is configured to determine whether an abnormality occurs based on a diffraction pattern measured by the plurality of pixels.

16. The abnormality detector according to claim 12, wherein the light detector includes a plurality of pixels configured to receive the diffracted light, wherein the determination unit including a differentiator configured to spatially differentiate data measured by the plurality of pixels, and wherein the determination unit is configured to determine whether occurs an abnormality based on an output of the differentiator.

17. The abnormality detector according to claim 16, wherein the data from the plurality of pixels are sequentially read, wherein the differentiator is configured to temporally differentiate the data sequentially read from the plurality of pixels, and wherein the determination unit is configured to determine that an abnormality occurs when the output of the differentiator exceeds a predetermined threshold.

18. The abnormality detector according to claim 12, further comprising:

a pinhole provided between the diffraction element and the light source.

19. The abnormality detector according to claim 18, wherein the light source and the abnormality detector are used for a vehicle lamp device, wherein the vehicle lamp device includes a reflector configured to reflect the output light of the light source, and wherein the reflector is formed with the pinhole.

20. The abnormality detector according to claim 12, wherein the diffraction element is configured to form an interference fringe when a coherent light is incident thereto.

* * * * *

UNITED STATES PATENT AND TRADEMARK OFFICE
CERTIFICATE OF CORRECTION

PATENT NO.       : 9,880,106 B2
APPLICATION NO.  : 14/845918
DATED            : January 30, 2018
INVENTOR(S)      : Tomoyuki Ichikawa It is certified that error appears in the above-identified patent and that said Letters Patent is hereby corrected as shown below:

On the Title Page

Item [73], the word "MANAUFACTURING" should read --MANUFACTURING--.

In the Claims

Column 19, Claim 3, Line 29, the word "claim" should read --claim 1--.

Signed and Sealed this
Fourth Day of September, 2018

Andrei Iancu
*Director of the United States Patent and Trademark Office*